(12) United States Patent
Zhang et al.

(10) Patent No.: US 12,391,711 B2
(45) Date of Patent: Aug. 19, 2025

(54) TETRAHYDROCANNABINOL DERIVATIVES, PREPARATION METHOD THEREOF AND USE THEREOF

(71) Applicant: CHENGDU BAIYU PHARMACEUTICAL CO., LTD., Sichuan (CN)

(72) Inventors: Jing Zhang, Chengdu (CN); Xuezhen Xu, Chengdu (CN); Yonggang Wei, Chengdu (CN); Hongzhu Chu, Chengdu (CN); Fuqiang Zhao, Chengdu (CN); Guizhuan Su, Chengdu (CN); Meiwei Wang, Chengdu (CN); Yi Sun, Chengdu (CN)

(73) Assignee: Chengdu Baiyu Pharmaceutical Co., Ltd., Chengdu (CN)

( * ) Notice: Subject to any disclaimer, the term of this patent is extended or adjusted under 35 U.S.C. 154(b) by 691 days.

(21) Appl. No.: 17/772,993

(22) PCT Filed: Jan. 7, 2021

(86) PCT No.: PCT/CN2021/070729
§ 371 (c)(1),
(2) Date: Apr. 28, 2022

(87) PCT Pub. No.: WO2021/139740
PCT Pub. Date: Jul. 15, 2021

(65) Prior Publication Data
US 2023/0227482 A1 Jul. 20, 2023

(30) Foreign Application Priority Data
Jan. 8, 2020 (CN) .......................... 202010016989.0

(51) Int. Cl.
*C07F 9/655* (2006.01)
(52) U.S. Cl.
CPC ...... *C07F 9/65522* (2013.01); *C07B 2200/05* (2013.01)
(58) Field of Classification Search
CPC .......................... C07F 9/65522; C07B 2200/05
See application file for complete search history.

(56) References Cited

U.S. PATENT DOCUMENTS

| | | | |
|---|---|---|---|
| 4,833,073 A | 5/1989 | McNally et al. | |
| 5,227,537 A | 7/1993 | Stoss et al. | |
| 6,008,383 A | 12/1999 | Elsohly et al. | |
| 6,274,635 B1 | 8/2001 | Travis | |
| 2003/0232101 A1 | 12/2003 | Travis | |
| 2005/0020544 A1 | 1/2005 | Garzon et al. | |
| 2006/0194761 A1 | 8/2006 | Gu | |
| 2007/0093665 A1 | 4/2007 | Burdick et al. | |
| 2009/0143462 A1 | 6/2009 | Stinchcomb et al. | |
| 2010/0298579 A1 | 11/2010 | Steup et al. | |
| 2015/0258040 A1 | 9/2015 | Lynch et al. | |
| 2015/0343071 A1 | 12/2015 | Vangara et al. | |
| 2016/0310443 A1 | 10/2016 | Reillo et al. | |
| 2017/0008868 A1 | 1/2017 | Dialer et al. | |
| 2017/0044092 A1 | 2/2017 | Appendino et al. | |
| 2019/0031601 A1 | 1/2019 | ElSohly et al. | |
| 2020/0181051 A1 | 6/2020 | McKinney | |
| 2023/0002425 A1 | 1/2023 | Xu et al. | |
| 2023/0059087 A1 | 2/2023 | Zhou et al. | |

FOREIGN PATENT DOCUMENTS

| | | | | |
|---|---|---|---|---|
| CN | 1331687 | * | 1/2002 | .......... C07D 311/80 |
| CN | 109400645 A | | 3/2019 | |
| EP | 4088723 A1 | | 11/2022 | |
| WO | 2004/016254 A2 | | 2/2004 | |
| WO | 2008/107879 A1 | | 9/2008 | |
| WO | 2018/096504 A1 | | 5/2018 | |
| WO | WO 2020117288 A1 | | 6/2020 | |
| WO | WO 2021046636 A1 | | 3/2021 | |

OTHER PUBLICATIONS

Gläser et al., "The Diels-Alder Approach to Δ⁹-Tetrahydrocannabinol Derivatives," *Eur. J. Org. Chem.* 2015(7):1516-1524, Mar. 2015.

(Continued)

*Primary Examiner* — Erich A Leeser
(74) *Attorney, Agent, or Firm* — Seed IP Law Group LLP

(57) ABSTRACT

Tetrahydrocannabinol derivatives and medical use thereof, in particular to the compounds represented by general formula (I), or stereoisomers, solvates, metabolites, pharmaceutically acceptable salts or cocrystals thereof, wherein the definitions of substituents in general formula (I) are the same as those in the description General formula (I)

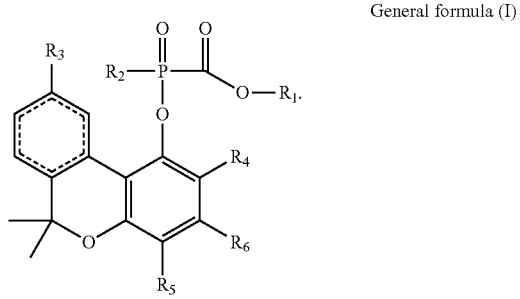

7 Claims, No Drawings

(56) References Cited

OTHER PUBLICATIONS

International Search Report for international application No. PCT/CN2021/070728, mailed Apr. 6, 2021, 3 pages (English translation).
International Search Report for international application No. PCT/CN2021/070729, mailed Apr. 9, 2021, 3 pages (English translation).
International Search Report for international application No. PCT/CN2021/070730, mailed Apr. 6, 2021, 3 pages (English translation).
Lago-Fernandez et al., "New Methods for the Synthesis of Cannabidiol Derivatives," Chapter Eleven, *Methods in Enzymology* 593:237-257, 2017.
Rong et al., "Review on Pharmacological Effects of Tetrahydrocannabinol and Cannabidiol," *Nat. Prod. Res. Dev.* 29:1449-1453, 2017 (with English abstract).
Sun et al., "Deuterium isotope effects in drug pharmacokinetics II: Substrate-dependence of the reaction mechanism influences outcome for cytochrome P450 cleared drugs," *PLoS ONE* 13(11):e0206279, p. 1-17, Nov. 14, 2018.
Pop et al., "Water-soluble combinations of dexanabinol: prodrugs and analogs," *Pharmazie* 55(3):167-171, Mar. 2000. (5 pages).

\* cited by examiner

TETRAHYDROCANNABINOL DERIVATIVES, PREPARATION METHOD THEREOF AND USE THEREOF

TECHNICAL FIELD

The present application relates to tetrahydrocannabinol derivatives, or stereoisomers, solvates, pharmaceutically acceptable salts or cocrystals thereof, and a pharmaceutical composition comprising the tetrahydrocannabinol derivatives, or stereoisomers, solvates, pharmaceutically acceptable salts or cocrystals thereof, and use thereof in preparing a medicament.

BACKGROUND

As an annual herbaceous plant of *Cannabis* in Moraceae, hemp (*Cannabis sativa* L.) is originated in Central Asia and East Asia and is widely distributed in the United States, India, Brazil etc. Hemp has been used as a medicament for a long history, however, due to the addiction and hallucinogenic effect of hemp, its clinical application has been greatly limited. There are hundreds of different chemicals in hemp, and about 70 chemicals among them are named as cannabinoids, which mainly comprise cannabidiol (CBD), cannabinol (CBN), tetrahydrocannabinol (THC) and homologues thereof. THC has a wide range of therapeutical effects and can significantly improve symptoms associated with neurological diseases. In addition, it shows promising application prospect in anti-tumor, anti-inflammatory, hepatoprotective, anti-pain, anti-anxiety, anti-insomnia, anti-convulsion, anti-vomiting, anti-spasm, anti-oxidation and neuroprotection. However, due to the low oral bioavailability of THC (human oral bioavailability is about 4%-12%) (Pain Res. Manag., 2005; 10: 15A-22A), it is necessary to develop new technologies to improve the absorption, distribution, transport and metabolism of the medicament in vivo, so as to improve the bioavailability and the selectivity of the medicament on target sites, reduce toxic and side effects of the medicament, and prolong the action time of the medicament, etc.

SUMMARY OF THE INVENTION

One object of the present application is to provide tetrahydrocannabinol derivatives, or stereoisomers, solvates, metabolites, pharmaceutically acceptable salts, cocrystals or prodrugs thereof. Another object of the present application is to provide a pharmaceutical composition comprising the tetrahydrocannabinol derivatives, or stereoisomers, solvates, metabolites, pharmaceutically acceptable salts, cocrystals or prodrugs thereof. Yet another object is to provide use of the above compounds or the composition in preparing a medicament.

In one or more embodiments of the present application, the compounds can be converted into their parent drugs after being ingested. When compared with the parent drugs, the compounds according to the present invention show higher bioavailability (e.g., oral bioavailability), longer half-life, improved therapeutic effects and reduced toxic and side effects.

One or more embodiments of the present application provide a compound represented by general formula (I), or stereoisomers, solvates, metabolites, pharmaceutically acceptable salts or cocrystals thereof:

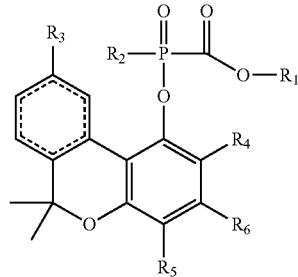

(I)

wherein:
$R_1$ is $C_{1-6}$ alkyl;
$R_2$ is

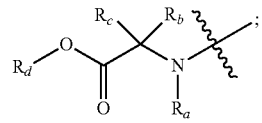

$R_3$ is selected from the group consisting of methyl, $C_{3-8}$ carbocyclic group, $-CH_2OH$, carboxyl, $-C(=O)OC_{1-6}$ alkyl and $-C(=O)NR^{b1}R^{b2}$;
$R_4$ and $R_5$ are each independently selected from the group consisting of H, halogen and carboxyl;
$R_a$ is selected from the group consisting of H and $C_{1-6}$ alkyl;
$R_b$ and $R_c$ are each independently selected from the group consisting of H, $C_{1-6}$ alkyl, amino acid side chain, $-C_{1-6}$ alkylene-$C_{3-12}$ carbocyclic ring and $-C_{1-6}$ alkylene-$C_{3-12}$ heterocyclic ring; the $C_{3-12}$ heterocyclic ring contains 1 to 4 heteroatoms selected from the group consisting of N, O and S; the $C_{1-6}$ alkylene, the $C_{1-6}$ alkyl, the $C_{3-12}$ carbocyclic ring and the $C_{3-12}$ heterocyclic ring are optionally further substituted by 0 to 3 substituents selected from the group consisting of hydroxyl, carboxyl, halogen, cyano, $=O$, $C_{1-6}$ alkyl, $C_{1-6}$ heteroalkyl, $C_{2-6}$ alkenyl, $C_{2-6}$ alkynyl, $-NR^{b1}R^{b2}$, $-C(=O)OC_{1-6}$ alkyl, $-C(=O)NR^{b1}R^{b2}$, $C_{3-12}$ cycloalkyl, $C_{3-12}$ heterocycloalkyl, $C_{6-12}$ aryl and $C_{5-12}$ heteroaryl; and the $C_{1-6}$ alkyl, the $C_{1-6}$ heteroalkyl, the $C_{2-6}$ alkenyl or the $C_{2-6}$ alkynyl are optionally further substituted by one or more groups selected from the group consisting of hydroxyl, carboxyl, cyano, halogen, $-O-R^{b1}$, $-NR^{b1}R^{b2}$, $C_{3-12}$ cycloalkyl, $C_{3-12}$ heterocycloalkyl, $C_{6-12}$ aryl and $C_{5-12}$ heteroaryl; when the amino acid side chain contains hydroxyl, mercapto or carboxyl, the hydroxyl, mercapto or carboxyl is optionally esterified;
$R^{b1}$ and $R^{b2}$ are each independently selected from the group consisting of H, $C_{1-6}$ alkyl, $-C(=O)R^{b3}$ and $-C(=O)NR^{b4}R^{b5}$, wherein the $C_{1-6}$ alkyl is optionally further substituted by one or more substituents selected from the group consisting of hydroxyl, halogen, $C_{1-6}$ alkyl, $C_{1-6}$ alkoxy, $C_{6-12}$ aryl, $C_{5-12}$ heteroaryl, $C_{3-12}$ cycloalkyl and $C_{3-12}$ heterocycloalkyl;
$R^{b3}$ is selected from the group consisting of $C_{1-6}$ alkyl, $C_{1-6}$ alkoxy and $C_{6-12}$ aryl;
$R^{b4}$ and $R^{b5}$ are each independently selected from the group consisting of H and $C_{1-6}$ alkyl; or $R^{b4}$ and $R^b$s together with N atom form a 3 to 12 membered heterocyclic ring containing 1 to 4 heteroatoms selected from the group consisting of N, O and S;

or, $R_b$ and $R_c$ together with the atom to which they are attached form a 3 to 6 membered carbocyclic ring or a 3 to 6 membered heterocyclic ring, the 3 to 6 membered carbocyclic ring or the 3 to 6 membered heterocyclic ring is optionally further substituted by 0 to 3 substituents selected from the group consisting of F, Cl, Br, I, hydroxyl, carboxyl and amino, wherein the 3 to 6 membered heterocyclic ring contains 1 to 4 heteroatoms selected from the group consisting of N, O and S;

$R_d$ is selected from the group consisting of $C_{1-6}$ alkyl, $C_{2-6}$ alkenyl, $C_{2-6}$ alkynyl, $C_{3-10}$ carbocyclic ring, 3 to 10 membered heterocyclic ring, —$C_{1-6}$ alkylene-$C_{3-10}$ carbocyclic ring, —$C_{1-6}$ alkylene-3 to 10 membered heterocyclic ring, —$C_{1-6}$ alkylene-O—$C_{1-6}$ alkylene-$C_{3-10}$ carbocyclic ring, —$C_{1-6}$ alkylene-O—$C_{1-6}$ alkylene-3 to 10 heterocyclic ring and —$C_{1-6}$ alkylene-O—$C_{1-4}$ alkyl; the $C_{1-6}$ alkylene, the $C_{2-6}$ alkenyl, the $C_{2-6}$ alkynyl, the $C_{1-6}$ alkyl, the $C_{3-10}$ carbocyclic ring and the 3 to 10 membered heterocyclic ring are optionally further substituted with 0 to 4 substituents selected from the group consisting of H, F, Cl, Br, I, hydroxyl, carboxyl, amino, 1-cyclopropylethyl, $C_{1-4}$ alkyl, $C_{1-4}$ alkoxy, —OC(=O)OR$_{d1}$ and —OC(=O)R$_{d2}$, wherein the 3 to 10 membered heterocyclic ring contains 1 to 6 heteroatoms selected from the group consisting of N, O and S;

$R_{d1}$ and $R_{d2}$ are each independently selected from the group consisting of $C_{1-4}$ alkyl, $C_{3-10}$ carbocyclic ring or 3 to 10 membered heterocyclic ring, the $C_{1-4}$ alkyl, $C_{3-10}$ carbocyclic ring and the 3 to 10 membered heterocyclic ring is optionally further substituted with 0 to 4 substituents selected from the group consisting of H, F, Cl, Br, I, hydroxyl, carboxyl, $C_{1-4}$ alkyl, $C_{1-4}$ alkoxy, $C_{3-10}$ carbocyclic ring and 3 to 10 membered heterocylic group, wherein the 3 to 10 membered heterocylic group contains 1 to 6 heteroatoms selected from the group consisting of N, O and S;

$R_6$ is selected from the group consisting of $C_{1-12}$ alkyl, $C_{1-12}$ heteroalkyl, $C_{2-12}$ alkenyl, $C_{2-12}$ alkynyl, $C_{1-12}$ alkylene, $C_{3-12}$ carbocyclic group, $C_{3-12}$ heterocyclic group, —$C_{1-6}$ alkylene-$C_{3-12}$ carbocyclic group, —$C_{1-6}$ alkylene-$C_{3-12}$ heterocyclic group, —NR$^{b1}$R$^{b2}$, —$C_{1-6}$ alkylene-C(=O)OC$_{1-6}$ alkyl and —$C_{1-6}$ alkylene-C(=O)NR$^{b1}$R$^{b2}$, and the $C_{1-12}$ alkyl, the $C_{1-12}$ heteroalkyl, the $C_{2-12}$ alkenyl, the $C_{2-12}$ alkynyl, the $C_{1-12}$ alkylene, the $C_{3-12}$ carbocyclic group and the $C_{3-12}$ heterocyclic group are optionally substituted with one or more substituents selected from the group consisting of hydroxyl, carboxyl, halogen, cyano, =O, $C_{1-6}$ alkyl, —NR$^{b1}$R$^{b2}$, $C_{3-12}$ carbocyclic group, $C_{3-12}$ heterocyclic group, $C_{2-6}$ alkenyl, $C_{2-6}$ alkynyl, —C(=O)OC$_{1-6}$ alkyl, —C(=O)C$_{1-6}$ alkyl, —C(=O)NR$^{b1}$R$^{b2}$, —S(=O)C$_{1-6}$ alkyl and —S(=O)$_2$C$_{1-6}$ alkyl, wherein as substituents, the $C_{1-6}$ alkyl, the $C_{3-12}$ carbocyclic group and the $C_{3-12}$ heteracyclic group are optionally further substituted with one or more substituents selected from the group consisting of =O, hydroxyl, carboxyl, halogen, cyano, —C(=O)OC$_{1-6}$ alkyl and —C(=O)C$_{1-6}$ alkyl;

═══ is a single bond or a double bond;

or, the general formula (I) is optionally substituted with one or more D atoms.

One or more embodiments of the present application provide a compound represented by general formula (II), or stereoisomers, solvates, metabolites, pharmaceutically acceptable salts or cocrystals thereof:

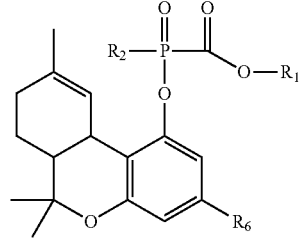

(II)

wherein, $R_1$ is $C_{1-6}$ alkyl;

$R_2$ is

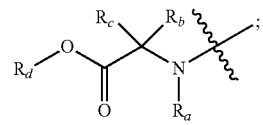

$R_a$ is H;

$R_b$ and $R_c$ are each independently selected from the group consisting of H and amino acid side chain; when the amino acid side chain contains hydroxyl, mercapto or carboxyl, the hydroxyl, mercapto or carboxyl is optionally esterified;

$R_d$ is selected from the group consisting of $C_{1-6}$ alkyl, —$C_{3-10}$ carbocyclic ring and 3 to 10 membered heterocyclic ring, wherein the $C_{1-6}$ alkyl, the —$C_{3-10}$ carbocyclic ring or the 3 to 10 membered heterocyclic ring is optionally further substituted with 0 to 4 substituents selected from the group consisting of H, F, Cl, Br, I, hydroxyl, carboxyl, amino, 1-cyclopropylethyl, $C_{1-4}$ alkyl, $C_{1-4}$ alkoxyl, OC(=O)OR$_{d1}$ and OC(=O)R$_{d2}$, wherein the 3 to 10 membered heterocyclic ring contains 1 to 6 heteroatoms selected from the group consisting of N, O and S;

$R_{d1}$ and $R_{d2}$ are each independently $C_{1-4}$ alkyl;

$R_6$ is selected from the group consisting of $C_{1-12}$ alkyl, $C_{3-12}$ carbocyclic group, and $C_{3-12}$ heterocyclic group, wherein the $C_{1-12}$ alkyl, the $C_{3-12}$ carbocyclic group and the $C_{3-12}$ heterocyclic group are optionally substituted by one or more substituents selected from the group consisting of hydroxyl, carboxyl, halogen, cyano, =O, $C_{1-6}$ alkyl, —NR$^{b1}$R$^{b2}$, $C_{3-12}$ carbocyclic group, $C_{3-12}$ heterocyclic group, $C_{2-6}$ alkenyl group, $C_{2-6}$ alkynyl group, —C(=O)OC$_{1-6}$ alkyl, —C(=O)C$_{1-6}$ alkyl, —C(=O)N$^{b1}$R$^{b2}$, —S(=O)C$_{1-6}$ alkyl and —S(=O)$_2$C$_{1-6}$ alkyl, wherein as substituents, the $C_{1-6}$ alkyl, the $C_{3-12}$ carbocylic group, the $C_{3-12}$ heterocyclic group are optionally substituted by one or more substituents selected from the group consisting of =O, hydroxyl, carboxyl, halogen, cyano, —C(=O)OC$_{1-6}$ alkyl and —C(=O)C$_{1-6}$ alkyl.

$R^{b1}$ and $R^{b2}$ are each independently selected from the group consisting of H, $C_{1-6}$ alkyl, —C(=O)R$^{b3}$ and —C(=O)NR$^{b4}$R$^{b5}$, wherein the $C_{1-6}$ alkyl is optionally further substituted by one or more substituents selected from the group consisting of hydroxyl, halogen, $C_{1-6}$ alkyl, $C_{1-6}$ alkoxy, $C_{6-12}$ aryl, $C_{5-12}$ heteroaryl, $C_{3-12}$ cycloalkyl and $C_{3-12}$ heterocycloalkyl;

$R^{b3}$ is selected from the group consisting of $C_{1-6}$ alkyl, $C_{1-6}$ alkoxy and $C_{6-12}$ aryl;

$R^{b4}$ and $R^{b5}$ are each independently selected from the group consisting of H and $C_{1-6}$ alkyl; or $R^{b4}$ and $R^{b5}$ together with N atom form a 3 to 12 membered heterocyclic ring containing 1 to 4 heteroatoms selected from the group consisting of N, O and S;

or, the general formula (II) can be optionally substituted by one or more D atoms.

One or more embodiments of the present application provide a compound represented by general formula (III), or stereoisomers, solvates, metabolites, pharmaceutically acceptable salts or cocrystals thereof:

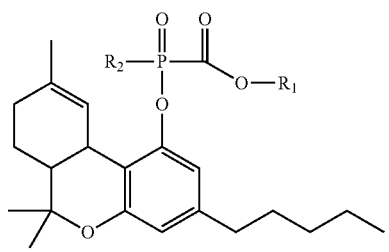
(III)

wherein, $R_1$ is $C_{1-6}$ alkyl;

$R_2$ is

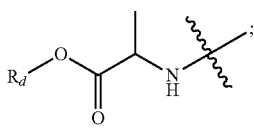

$R_d$ is selected from the group consisting of $C_{1-6}$ alkyl, —$C_{3-10}$ carbocyclic group and 3 to 10 membered heterocyclic group, wherein the $C_{1-6}$ alkyl, the —$C_{3-10}$ carbocyclic group or the 3 to 10 membered heterocyclic group is optionally further substituted with 0 to 4 substituents selected from the group consisting of H, F, Cl, Br, I, hydroxyl, carboxyl, amino, 1-cyclopropyl-ethyl, $C_{1-4}$ alkyl, $C_{1-4}$ alkoxyl, OC(=O)O$R_{d1}$ and OC(=O)$R_{d2}$, wherein the 3 to 10 membered heterocyclic group contains 1 to 6 heteroatoms selected from the group consisting of N, O and S;

$R_{d1}$ and $R_{d2}$ are each independently $C_{1-4}$ alkyl;

or, the general formula (III) is optionally substituted with one or more D atoms.

One or more embodiments of the present application provide a compound, or stereoisomers, solvates, metabolites, pharmaceutically acceptable salts or cocrystals thereof, wherein the compound is one of the following:

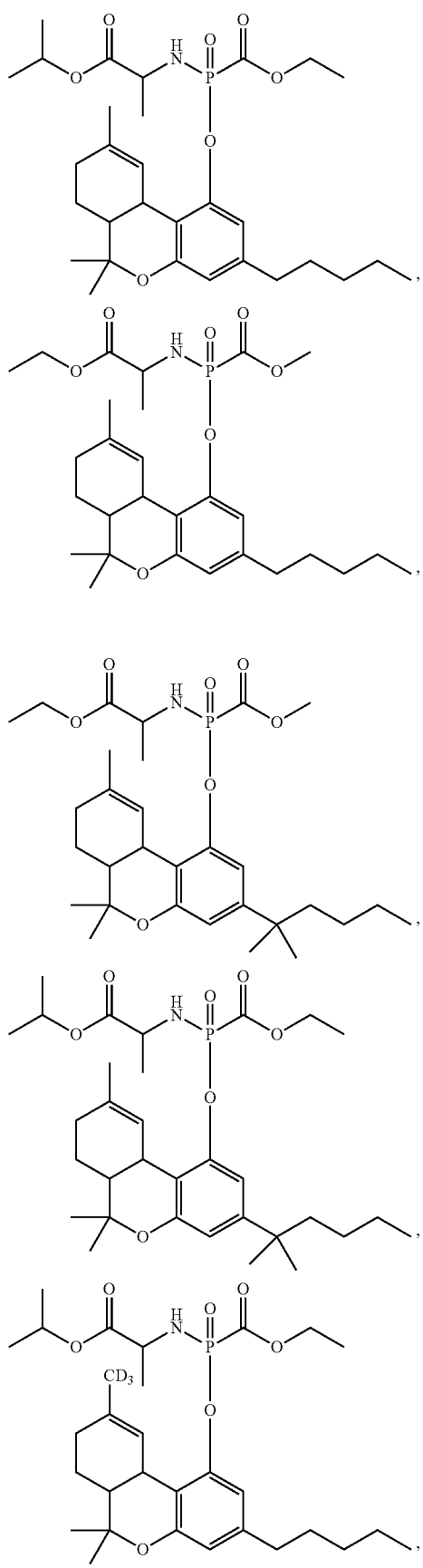

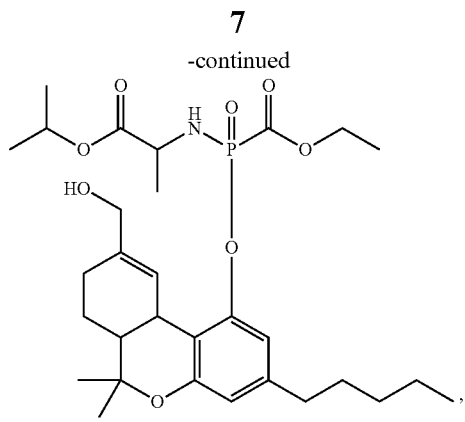
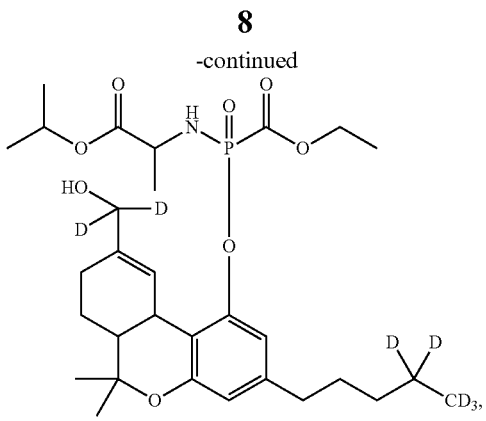
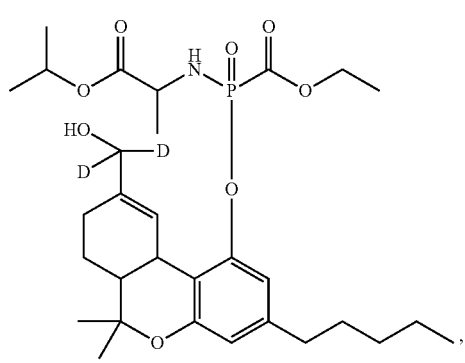
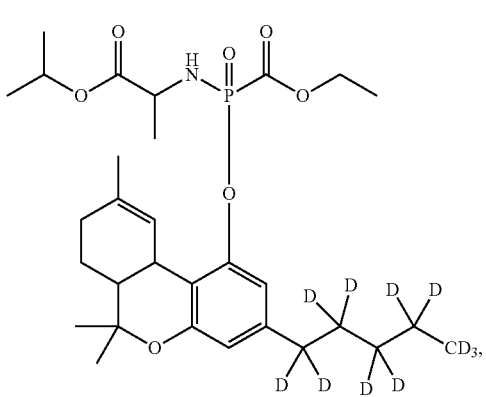
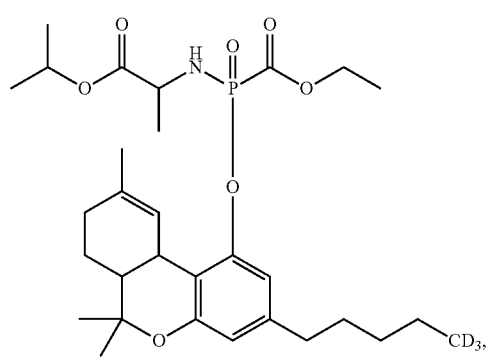
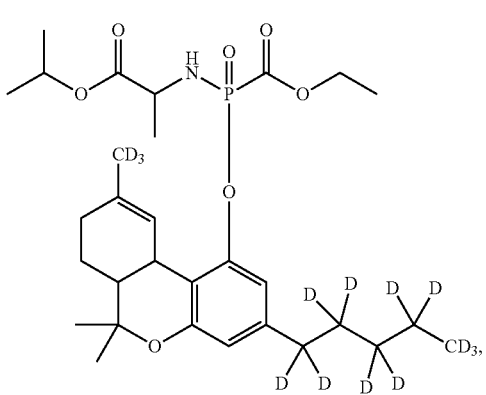
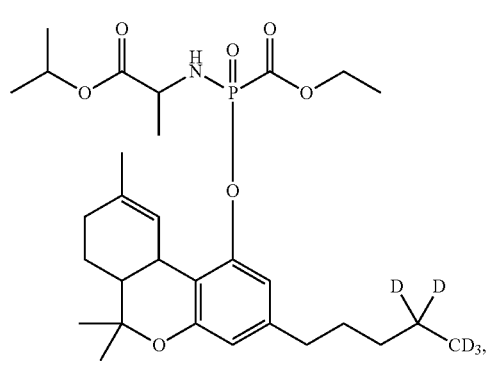
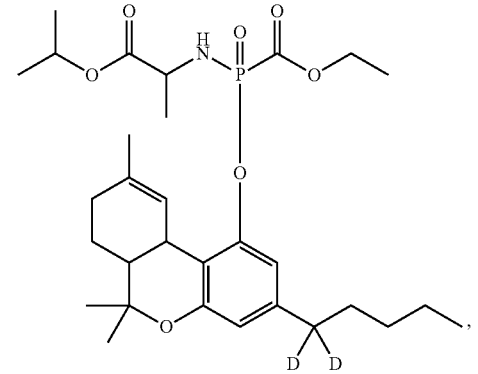

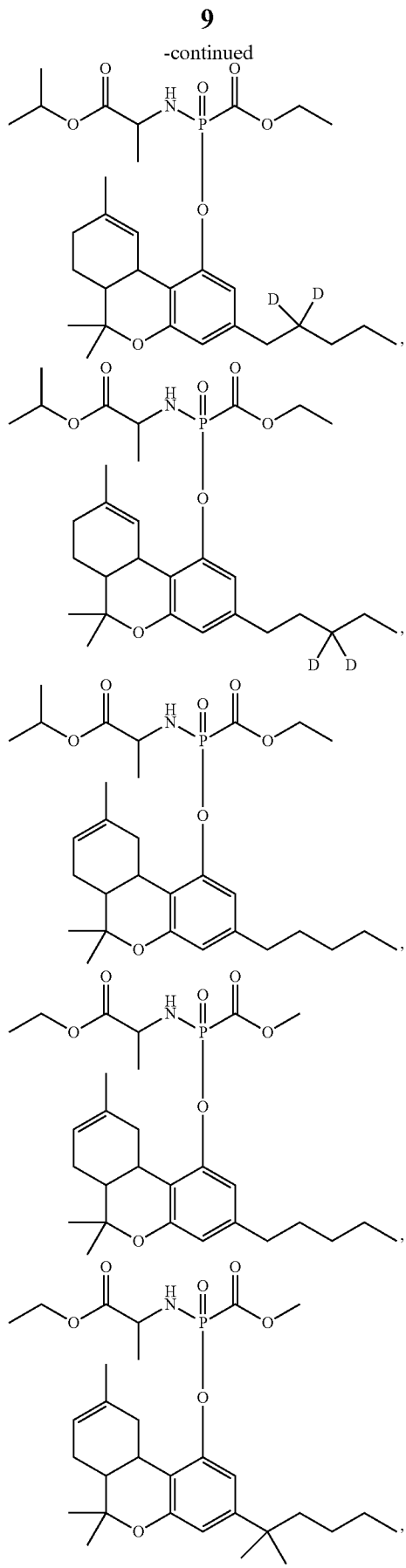
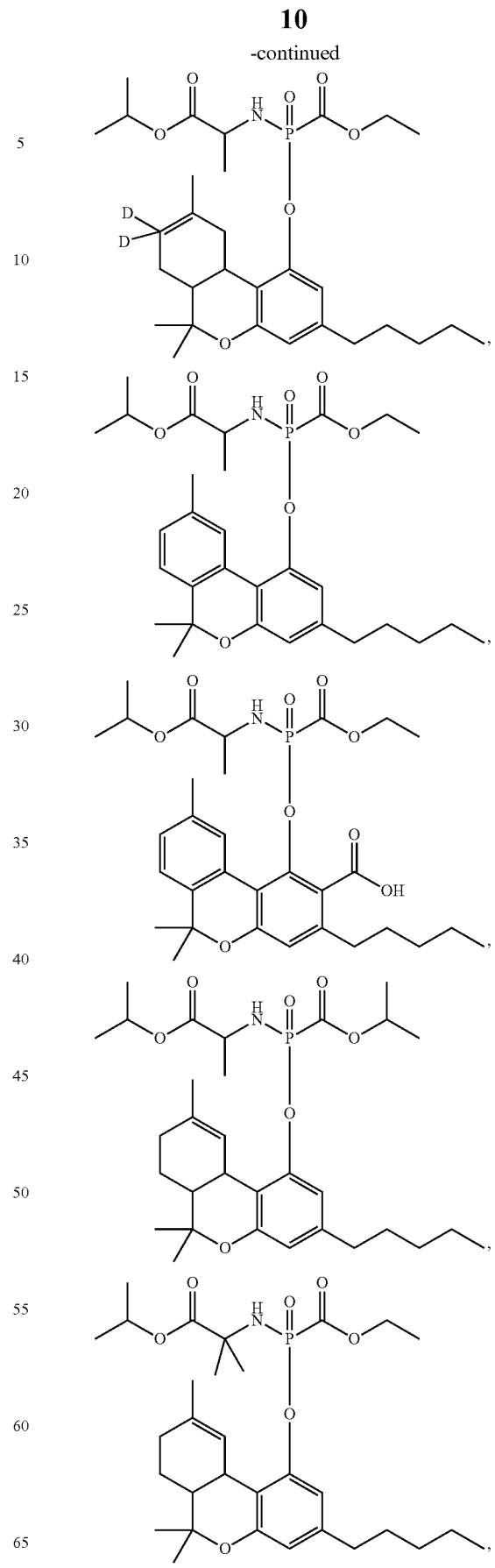

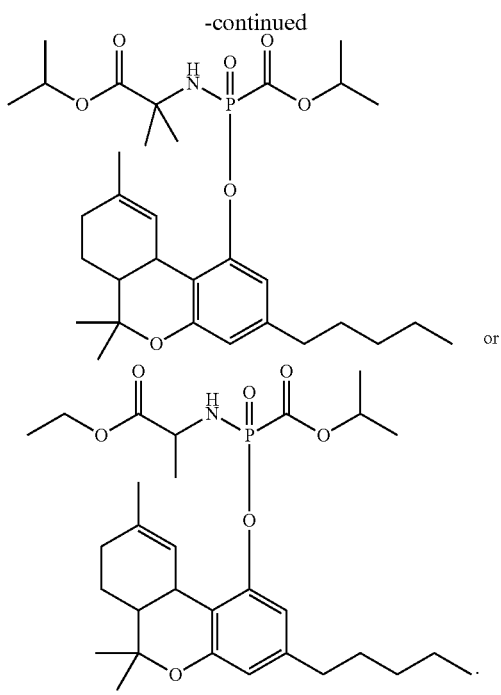

One or more embodiments of the present application provide a pharmaceutical composition comprising:
(1) the compound according to the present application, or stereoisomers, solvates, metabolites, pharmaceutically acceptable salts or cocrystals thereof;
(2) optional one or more other active ingredients; and
(3) a pharmaceutically acceptable carrier and/or excipient.

In one or more embodiments of the present application, the other active ingredient is one or more selected from the group consisting of ginkgolides, antineoplastic agents, anticoagulants, antiepileptic agents, antidepressants, anxiolytics, hypnotics, analgesics and anesthetics, or stereoisomers, hydrates, metabolites, solvates, pharmaceutically acceptable salts or cocrystals thereof.

In one or more embodiments of the present application, the ginkgolide is one of ginkgolide A, ginkgolide B, ginkgolide C, ginkgolide D, ginkgolide J, ginkgolide M, ginkgolide K, ginkgolide L, ginkgolide N, ginkgolide P, ginkgolide Q or combinations of two or more thereof in any ratio.

One or more embodiments of the present application provide use of the compound according to the present application, or stereoisomers, solvates, metabolites, pharmaceutically acceptable salts or cocrystals thereof or a pharmaceutical composition comprising the compound in the preparation of medicament for treating post-traumatic stress disorder, facial paralysis, stroke, migraine, coronary heart disease stable angina pectoris, cerebral infarction, thromboembolism, myocardial infarction, cardiac ischemia, coronary artery disease, hypertension, cerebral ischemia, improvement of sexual function, spasm, acute and chronic pain, fibromyalgia, postoperative pain, cluster headache, tension headache, back pain, limbs pain, lumbago, neck pain, neuropathic pain, cancer pain, trigeminal neuralgia, arthritic pain, inflammatory pain, Dravet syndrome, Lennox-Gastaut syndrome, Prader-Willi syndrome, Sturge-Weber syndrome, fragile X syndrome, anxiety, bipolar affective disorder, autism, general anxiety disorder, social anxiety disorder, epilepsy, Parkinson's disease, Alzheimer's disease, Huntington's disease, opioid abuse, alcoholism, nicotine addiction, anorexia, cachexia, chemotherapy-related nausea and vomiting, postoperative nausea and vomiting, amyotrophic lateral sclerosis (ALS), Friedreich ataxia, schizophrenia, obsessive-compulsive disorder, multiple sclerosis, depression, sleep disorder, spasm caused by multiple sclerosis, dysmyotonia, sleep apnea, paralytic dementia, hypomnesis or glioblastoma.

One or more embodiments of the present application provide the above compounds, or stereoisomers, solvates, metabolites, pharmaceutically acceptable salts or cocrystals thereof of the present application for use as a medicament.

One or more embodiments of the present application provide the above compound according to the present application, or stereoisomers, solvates, metabolites, pharmaceutically acceptable salts or cocrystals thereof used in a method for treating the following disease: post-traumatic stress disorder, facial paralysis, stroke, migraine, coronary heart disease stable angina pectoris, cerebral infarction, thromboembolism, myocardial infarction, cardiac ischemia, coronary artery disease, hypertension, cerebral ischemia, improvement of sexual function, spasm, acute and chronic pain, fibromyalgia, postoperative pain, cluster headache, tension headache, back pain, limbs pain, lumbago, neck pain, neuropathic pain, cancer pain, trigeminal neuralgia, arthritic pain, inflammatory pain, Dravet syndrome, Lennox-Gastaut syndrome, Prader-Willi syndrome, Sturge-Weber syndrome, fragile X syndrome, anxiety, bipolar affective disorder, autism, general anxiety disorder, social anxiety disorder, epilepsy, Parkinson's disease, Alzheimer's disease, Huntington's disease, opioid abuse, alcoholism, nicotine addiction, anorexia, cachexia, chemotherapy-related nausea and vomiting, postoperative nausea and vomiting, amyotrophic lateral sclerosis (ALS), Friedreich ataxia, schizophrenia, obsessive-compulsive disorder, multiple sclerosis, depression, sleep disorder, spasm caused by multiple sclerosis, dysmyotonia, sleep apnea, paralytic dementia, hypomnesis or glioblastoma.

One or more embodiments of the present application provide a method for treating the following disease, comprising administering to a subject in need thereof the above compound according to the present application, or stereoisomers, solvates, metabolites, pharmaceutically acceptable salts or cocrystals thereof: post-traumatic stress disorder, facial paralysis, stroke, migraine, coronary heart disease stable angina pectoris, cerebral infarction, thromboembolism, myocardial infarction, cardiac ischemia, coronary artery disease, hypertension, cerebral ischemia, improvement of sexual function, spasm, acute and chronic pain, fibromyalgia, postoperative pain, cluster headache, tension headache, back pain, limbs pain, lumbago, neck pain, neuropathic pain, cancer pain, trigeminal neuralgia, arthritic pain, inflammatory pain, Dravet syndrome, Lennox-Gastaut syndrome, Prader-Willi syndrome, Sturge-Weber syndrome, fragile X syndrome, anxiety, bipolar affective disorder, autism, general anxiety disorder, social anxiety disorder, epilepsy, Parkinson's disease, Alzheimer's disease, Huntington's disease, opioid abuse, alcoholism, nicotine addiction, anorexia, cachexia, chemotherapy-related nausea and vomiting, postoperative nausea and vomiting, amyotrophic lateral sclerosis (ALS), Friedreich ataxia, schizophrenia, obsessive-compulsive disorder, multiple sclerosis, depression, sleep disorder, spasm caused by multiple sclerosis, dysmyotonia, sleep apnea, paralytic dementia, hypomnesis or glioblastoma.

Unless stated otherwise, the terms used in the description and claims have the following meanings.

The carbon, hydrogen, oxygen, sulfur, nitrogen or F, Cl, Br and I involved in the groups and compounds of the present application all comprise their isotopes, and the carbon, hydrogen, oxygen, sulfur or nitrogen involved in the groups and compounds of the present application are optionally further replaced by one or more corresponding isotopes, wherein carbon isotopes comprise $^{12}C$, $^{13}C$ and $^{14}C$, and hydrogen isotopes comprise protium (H), deuterium (D, also referred as heavy hydrogen), tritium (T, also referred as superheavy hydrogen); oxygen isotopes comprise $^{16}O$, $^{17}O$ and $^{18}O$, sulfur isotopes comprise $^{32}S$, $^{33}S$, $^{34}S$ and $^{36}S$, nitrogen isotopes comprise $^{14}N$ and $^{15}N$, fluorine isotopes comprise $^{17}F$ and $^{19}F$, chlorine isotopes comprise $^{35}Cl$ and $^{37}Cl$, and bromine isotopes comprise $^{79}Br$ and $^{81}Br$.

"Hydrocarbyl" refers to a group containing only carbon and hydrogen atoms.

"Alkyl" refers to a linear or branched saturated aliphatic hydrocarbyl having 1 to 20 carbon atoms. It is preferably an alkyl group having 1 to 8 (for example, 1, 2, 3, 4, 5, 6, 7, 8) carbon atoms, more preferably an alkyl group having 1 to 6 carbon atoms, and further preferably an alkyl group having 1 to 4 carbon atoms. Non-limiting examples thereof comprise methyl, ethyl, n-propyl, isopropyl, n-butyl, sec-butyl, neobutyl, tert-butyl, n-pentyl, isopentyl, neopentyl, n-hexyl and various branched isomers thereof, when the alkyl is substituted, it can be optionally further substituted by one or more substituents.

"Heteroalkyl" refers to a group in which at least one C atom of an alkyl is replaced by 0, S, N or P atom. Non-limiting examples thereof comprise thiomethyl, thioethyl, thio n-propyl, thioisopropyl, thio n-butyl, thio sec-butyl and thio tert-butyl. The definition of alkyl is the same as that of the "alkyl" mentioned above.

"Alkoxyl" refers to a group in which at least one C atom of an alkyl is replaced by oxygen atom. Non-limiting examples thereof comprise methoxy, ethoxy, n-propoxy, isopropoxy, n-butoxy, sec-butoxy, tert-butoxy, n-pentoxy, n-hexyloxy, cyclopropyloxy and cyclobutyloxy. The definition of alkyl is the same as that of the "alkyl" mentioned above.

"Alkenyl" refers to a straight or branched unsaturated aliphatic hydrocarbyl containing 1 to 10 (e.g., 1, 2, 3, 4, 5, 6, 7, 8, 9, 10) carbon-carbon double bonds and consisting of 2 to 20 carbon atoms, preferably 2 to 12 (e.g., 2, 3, 4, 5, 6, 7, 8, 9, 10, 11, 12) carbon atoms, more preferably 2 to 8 carbon atoms, even more preferably 2 to 6 carbon atoms. Non-limiting examples thereof comprise vinyl, propylen-2-yl, buten-2-yl, buten-2-yl, penten-2-yl, penten-4-yl, hexen-2-yl, hexen-3-yl, hepten-2-yl, hepten-3-yl, hepten-4-yl, octen-3-yl, nonen-3-yl, decen-4-yl and undecen-3-yl. The alkenyl may be optionally further substituted by one or more substituents.

"Alkynyl" refers to a straight or branched unsaturated aliphatic hydrocarbonyl containing 1 to 10 (e.g., 1, 2, 3, 4, 5, 6, 7, 8, 9 or 10) carbon-carbon triple bonds and consisting of 2 to 20 carbon atoms, preferably 2 to 12 (e.g., 2, 3, 4, 5, 6, 7, 8, 9, 10, 11 or 12) carbon atoms, more preferably 2 to 8 carbon atoms, even more preferably 2 to 6 carbon atoms. Non-limiting examples thereof comprise ethynyl, propyn-1-yl, propyn-2-yl, butyn-1-yl, butyn-2-yl, butyn-3-yl, 3,3-dimethylbutyn-2-yl, pentyn-1-yl, pentyn-2-yl, hexyn-1-yl, 1-heptyn-1-yl, heptyn-3-yl, heptyn-4-yl, octyne-3-yl, nonyn-3-yl, decyn-4-yl, undecyn-3-yl, and dodecyn-4-yl. The alkynyl may be optionally further substituted by one or more substituents.

"Aryl" refers to a substituted or unsubstituted aromatic ring, which can be 5 to 8 (e.g., 5, 6, 7, 8) membered monocyclic ring, a 5 to 12 (e.g., 5, 6, 7, 8, 9, 10, 11, 12) membered bicyclic ring, or a 10 to 15 (e.g., 10, 11, 12, 13, 14, 15) membered tricyclic system. The aryl can be a bridged ring or a spiro ring. Non-limiting examples thereof comprise phenyl and naphthyl. The aryl may be optionally further substituted by one or more substituents.

"Heteroaryl" refers to a substituted or unsubstituted aromatic ring, which can be a 3 to 8 (e.g., 3, 4, 5, 6, 7, 8) membered monocyclic ring, a 5 to 12 (e.g., 5, 6, 7, 8, 9, 10, 11, 12) membered bicyclic ring, or 10 to 15 (e.g., 10, 11, 12, 13, 14, 15) membered tricyclic ring system and contains 1 to 6 (e.g., 1, 2, 3, 4, 5, 6) heteroatoms selected from the group consisting of N, O and S. The heteroaryl is preferably a 5- to 8-membered heteroaryl. Optionally substituted 1 to 4 (for example, 1, 2, 3, 4) N and S in the ring of the heteroaryl can be oxidized to various oxidation states. The heteroaryl can be connected to a heteroatom or a carbon atom, and the heteroaryl can be bridged ring or spiro rings. Non-limiting examples thereof comprise pyridyl, furyl, thienyl, pyranyl, pyrrolyl, pyrimidinyl, pyrazinyl, pyridazinyl, imidazolyl, piperidinyl, benzimidazolyl, benzopyridyl and pyrrolopyridinyl. The heteroaryl may be optionally further substituted by one or more substituents.

"Carbocyclic group" or "carbocyclic ring" refers to saturated or unsaturated aromatic ring or non-aromatic ring. When it is an aromatic ring, its definition is the same as the above definition of "aryl"; when it is a non-aromatic ring, it can be a 3 to 10 (e.g., 3, 4, 5, 6, 7, 8, 9, 10) membered monocyclic ring, a 4 to 12 (e.g., 4, 5, 6, 7, 8, 9, 10, 11, 12) membered bicyclic ring, or a 10 to 15 (e.g., 10, 11, 12, 13, 14, 15) membered tricyclic system. Non-limiting examples thereof comprise cyclopropyl, cyclobutyl, cyclopentyl, 1-cyclopent-1-enyl, 1-cyclopent-2-enyl, 1-cyclopent-3-enyl, cyclohexyl, 1-cyclohex-2-enyl, 1-cyclohex-3-enyl, cyclohexenyl, cyclohexadienyl, cycloheptyl, cyclooctyl, cyclononyl, cyclodecyl, cycloundecyl, cyclododecyl,

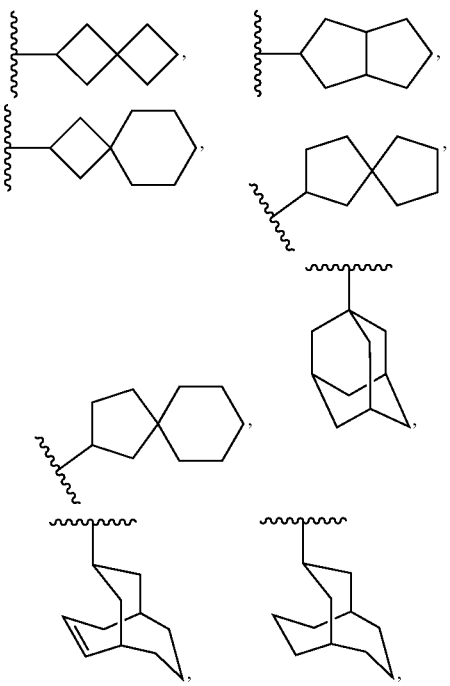

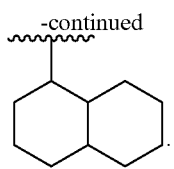

The "carbocyclic group" or "carbocyclic ring" may be optionally further substituted by one or more substituents.

"Heterocyclic group" or "heterocyclic ring" refers to saturated or unsaturated aromatic heterocyclic ring or non-aromatic heterocyclic ring. When it is aromatic heterocyclic ring, its definition is the same as that of the above "heteroaryl"; when it is a non-aromatic heterocyclic ring, it can be a 3 to 10 (e.g., 3, 4, 5, 6, 7, 8, 9, 10) membered monocyclic ring, a 4 to 12 (e.g., 4, 5, 6, 7, 8, 9, 10, 11, 12) membered bicyclic ring, or 10 to 15 (e.g., 10, 11, 12, 13, 14, 15) membered tricyclic ring system, and contains 1 to 4 (e.g., 1, 2, 3, 4) heteroatoms selected from the group consisting of N, O and S; Preferably it is a 3 to 8 membered heterocyclic group. Optionally substituted 1 to 4 (e.g., 1, 2, 3, 4) N or S in the ring of "heterocyclic group" or "heterocyclic ring" can be oxidized into various oxidation states; "heterocyclic group" or "heterocyclic ring" can be connected to a heteroatom or a carbon atom; "heterocyclic group" or "heterocyclic ring" can be a bridged ring or a spiro ring. Non-limiting examples thereof comprise oxiranyl, epoxypropyl, aziridinyl, oxetanyl, azetidinyl, thietanyl, 1,3-dioxolanyl, 1,4-dioxolanyl, 1,3-dioxanyl, azepanyl, oxepanyl, thiepanyl, oxazepinyl, diazepinyl, thiazepinyl, pyridyl, piperidinyl, homopiperidinyl, furyl, thienyl, pyranyl, N-alkylpyrrolyl, pyrimidinyl, pyridinyl, pyridazinyl, piperazinyl, homopiperazinyl, imidazolyl, piperidinyl, morpholinyl, thiomorpholinyl, thioxanyl, 1,3-dithianyl, dihydrofuranyl, dithiolanyl, tetrahydrofuranyl, tetrahydrothienyl, tetrahydropyranyl, tetrahydrothiopyranyl, tetrahydropyrrolyl, tetrahydroimidazolyl, tetrahydrothiazolyl, tetrahydropyranyl, benzimidazolyl, benzopyridyl, pyrrolopyridyl, benzodihydrofuranyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydrothienyl, pyrazolidinyl, imidazolinyl, imidazolidinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-indolylquinazinyl, N-pyridylurea, 1,1-dioxothiomorpholinyl, azabicyclo[3.2.1]octyl,

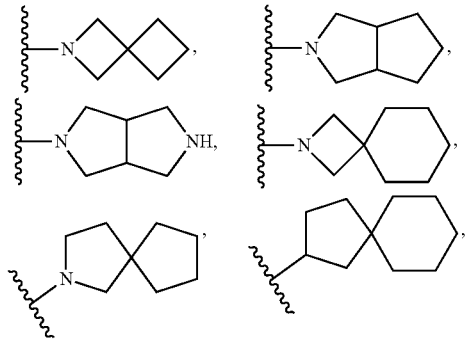

azabicyclo [5.2.0] nonyl, oxatricyclo[5.3.1.1]dodecyl, azaadamantyl and oxaspiro[3.3]heptyl. The "heterocyclic group" or "heterocyclic ring" may be optionally further substituted by one or more substituents.

"Cycloalkyl" refers to a saturated cyclic hydrocarbyl, which can be a 3 to 10 (e.g., 3, 4, 5, 6, 7, 8, 9, 10) membered monocyclic ring, a 4 to 12 (e.g., 4, 5, 6, 7, 8, 9, 10, 11, 12) membered bicyclic ring or 10 to 20 (e.g., 4, 5, 6, 7, 8, 9, 10, 11, 12) membered polycyclic ring system. There are preferably 3 to 10, more preferably 3 to 8 ring carbon atoms. Non-limiting examples of "cycloalkyl" comprise cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, 1,5-cyclooctadienyl, 1,4-cyclohexadienyl and cycloheptatrienyl, etc. When the cycloalkyl is substituted, it can be optionally further substituted by one or more substituents.

"Heterocycloalkyl" refers to a substituted or unsubstituted saturated non-aromatic ring group, which can be 3 to 8 (e.g., 3, 4, 5, 6, 7, 8) membered monocyclic ring, 4 to 12 (e.g., 4, 5, 6, 7, 8, 9, 10, 11, 12) membered bicyclic ring or 10 to 15 (e.g., 10, 11, 12, 13, 14, 15) membered tricyclic system, and contains 1, 2 or 3 heteroatoms selected from the group consisting of N, O and S. It is preferably a 3 to 8 membered heterocyclic group. Optionally substituted N or S in the ring of "heterocycloalkyl" can be oxidized to various oxidation states; "heterocycloalkyl" can be connected to a heteroatom or a carbon atom; and the "heterocycloalkyl" can be a bridged ring or a spiro ring. Non-limiting examples of "heterocycloalkyl" comprise oxiranyl, aziridinyl, oxetanyl, azetidinyl, 1,3-dioxolanyl, 1,4-dioxolanyl, 1,3-dioxanyl, azepanyl, piperidinyl, piperidinyl, morpholinyl, thiomorpholinyl, 1,3-dithianyl, tetrahydrofuranyl, tetrahydropyrrolyl, tetrahydroimidazolyl, tetrahydrothiazolyl, tetrahydropyranyl, azabicyclo[3.2.1]octyl, azabicyclo[5.2.0]nonyl, oxatricyclo[5.3.1.1]dodecyl, azaadamantyl and oxaspiro [3.3]heptyl.

When the above-mentioned "alkyl", "alkoxy", "alkenyl", "alkynyl", "aryl", "heteroaryl", "carbocyclic group", "carbocyclic ring", "heterocyclic group", "heterocyclic ring", "cycloalkyl", "heterocycloalkyl" or "heterocyclic group" are substituted, they may be optionally substituted with 0, 1, 2, 3, 4, 5, 6, 7, 8, 9 or 10 substituents selected from the group consisting of F, Cl, Br, I, hydroxyl, mercapto, nitro, cyano, amino, $C_{1-6}$ alkylamino, =O, $C_{1-6}$ alkyl, $C_{1-6}$ alkoxy, $C_{2-6}$ alkenyl, $C_{2-6}$ alkynyl, —$NR^{q4}R^{q5}$, =$NR^{q6}$, —C(=O)O$C_{1-6}$ alkyl, —OC(=O)$C_{1-6}$ alkyl, —C(=O)$NR^{q4}R^{q5}$, $C_{3-8}$ cycloalkyl, $C_{3-8}$ heterocycloalkyl, $C_{6-10}$ aryl, $C_{5-10}$ heteroaryl, —C(=O)O$C_{6-10}$ aryl, —OC(=O)$C_{6-10}$ aryl, —OC(=O)$C_{5-10}$ heteroaryl, —C(=O)O$C_{5-10}$ heteroaryl, —OC(=O)$C_{3-8}$ heterocycloalkyl, —C(=O)O$C_{3-8}$ heterocycloalkyl, —OC(=O)$C_{3-8}$ cycloalkyl, —C(=O)O$C_{3-8}$ cycloalkyl, —NHC(=O)$C_{3-8}$ heterocycloalkyl, —NHC(=O)$C_{6-10}$ aryl, —NHC(=O)$C_{5-10}$ heteroaryl, —NHC(=O)$C_{3-8}$ cycloalkyl, —NHC(=O)$C_{3-8}$ heterocycloalkyl, —NHC(=O)$C_{2-6}$ alkenyl or —NHC(=O)$C_{2-6}$ alkynyl, wherein the substituents $C_{1-6}$ alkyl, $C_{1-6}$ alkoxy, $C_{2-6}$ alkenyl, $C_{2-6}$ alkynyl, $C_{3-8}$ cycloalkyl, $C_{3-8}$ heterocycloalkyl, $C_{6-10}$ aryl, $C_{5-10}$ heteroaryl, —NHC(=O)$C_{6-10}$ aryl, —NHC(=O)$C_{5-10}$ heteroaryl, —NHC(=O)$C_{3-8}$ heterocycloalkyl or —NHC(=O)$C_{3-8}$ cycloalkyl can be optionally substituted with 1 to 3 substituents selected from the group consisting of OH, F, Cl, Br, I, $C_{1-6}$ alkyl, $C_{1-6}$ alkoxyl, —$NR^{q4}R^{q5}$ or =O. $R_{q1}$ is selected from the group consisting of $C_{1-6}$ alkyl, $C_{1-6}$alkoxyl or $C_{6-10}$ aryl; $R^{q2}$ or $R^{q3}$ is selected from the group consisting of H or $C_{1-6}$ alkyl; wherein, $R^{q4}$ and $R^{q5}$ are selected from the group consisting of H, $C_{1-6}$ alkyl, —NH(C=$NR^{q1}$)$NR^{q2}R^{q3}$, —S(=O)$_2$ $NR^{q2}R^{q3}$, —C(=O)$R^{q1}$ or —C(=O)$NR^{q2}R^{q3}$, and the $C_{1-6}$ alkyl is optionally substituted with one or more substituents selected from the group consisting of OH, F, Cl, Br, I, $C_{1-6}$ alkyl, $C_{1-6}$ alkoxy, $C_{6-10}$ aryl, $C_{5-10}$ heteroaryl, $C_{3-8}$ cycloalkyl, or $C_{3-8}$ heterocycloalkyl; or $R^{q4}$ and $R^{q5}$ together with N atom form 3 to 8 membered heterocyclic ring containing one or more heteroatoms selected from the group consisting of N, O and S.

"Amino acid side chain" refers to a group other than amino and carboxyl groups in an amino acid molecule.

"Pharmaceutically acceptable salt" or "pharmaceutically acceptable salt thereof" means that the compound of the present application maintains the biological effectiveness and characteristics of the free acid or free base, and the salts obtained by reacting the free acid with a non-toxic inorganic base or organic base, or the salts can be obtained by reacting the free base with a non-toxic inorganic acid or organic acid.

"Pharmaceutical composition" refers to a mixture of one or more compounds according to the present application, pharmaceutically acceptable salts or prodrugs thereof and other chemical components, wherein "other chemical components" refers to pharmaceutically acceptable carriers, excipients and/or one or more other therapeutic agents.

"Carrier" refers to a material that does not cause obvious irritation to organisms and does not eliminate the biological activity and characteristics of the administered compound.

"Excipient" refers to inert substances added to pharmaceutical compositions to facilitate the administration of compounds. Non-limiting examples thereof comprise calcium carbonate, calcium phosphate, sugar, starch, cellulose derivatives (including microcrystalline cellulose), gelatin, vegetable oil, polyethylene glycols, diluents, granulating agents, lubricants, adhesives and disintegrating agents.

"Prodrug" refers to a compound which can be converted into the compound according to the present application having biological activity by metabolism in vivo. The prodrugs of the present application can be prepared by modifying amino or carboxyl groups in the compound of the present application, and the modification can be removed by conventional operation or in vivo to obtain the parent compound. When the prodrug of the present application is administered to a mammalian subject, the prodrug is cleaved to form free amino groups or carboxyl groups.

"Cocrystal" refers to the crystal formed by the combinations of active pharmaceutical ingredients (API) and cocrystal former (CCF) under the action of hydrogen bonds or other noncovalent bonds, in which the pure states of API and CCF are both solid at room temperature, and there is a fixed stoichiometric ratio among the components. Cocrystal is a multi-component crystal, which comprises binary cocrystal formed between two neutral solids and multicomponent cocrystal formed by neutral solids and salts or solvates.

"Stereoisomers" refer to isomers produced by different spatial arrangement of atoms in molecules, including cis-trans isomers, enantiomers and conformational isomers.

"Optional", "optionally", "selective" or "selectively" means that the event or condition described subsequently can, but does not necessarily, occur, and the description comprises the situation in which the event or condition occurs and the situation in which the event or condition does not occur. For example, "heterocyclic group optionally substituted by alkyl" means that the alkyl group may, but does not necessarily exist, and the description comprises the situation where the heterocyclic group is substituted by alkyl, and the situation where the heterocyclic group is not substituted by alkyl.

Specific embodiments are described in detail in the description of the present application, and those skilled in the art should realize that the above embodiments are exemplary and cannot be understood as a limitation to the present application. Those skilled in the art can make improvements and modifications to the present application, without departing from the principle of the present application, the technical solutions obtained by these improvements and modifications also fall within the protection scope of the claims of the present application.

SPECIFIC EMBODIMENTS

The following examples will illustrate the technical solution of the present application in detail, and the scope of the present application comprises, but is not limited to the examples.

The structures of the compounds were determined by nuclear magnetic resonance (NMR) or/and mass spectrometry (MS). NMR shift (δ) was given in units of $10^{-6}$ (ppm). The NMR test was conducted by using nuclear magnetic instrument (Bruker Avance III 400 and Bruker Avance 300), and the solvent for the test was deuterated dimethyl sulfoxide (DMSO-$d_6$), deuterated chloroform (CDCl$_3$), deuterated methanol (CD$_3$OD), and the internal standard was tetramethylsilane (TMS).

MS test was conducted on Agilent 6120B(ESI) and Agilent 6120B(APCI);

HPLC test was conducted on Agilent 1260DAD high pressure liquid chromatograph (zorbax sb-C18 100×4.6 mm, 3.5 μm).

HSGF254 silica gel plate from Yantai Huanghai or Qingdao GF254 silica gel plate was used for thin layer chromatography (TLC), and the size of the silica gel plate for thin layer chromatography (TLC) was 0.15 mm to 0.20 mm, and the size of the silica gel plate for thin layer chromatography separation and purification products was 0.4 mm to 0.5 mm;

Silica gel of 200-300 mesh by Yantai Huanghai was generally used as carrier of the column chromatography.

The known starting materials in the present application can be synthesized by using the methods known in the field, or can be purchased from Titan Technology company, Annaiji Chemical company, Shanghai DEMO Medical Tech Co., Ltd, Chengdu Kelong Chemical company, Shaoyuan Chemical Technology company, Bailingwei Technology company, etc.

Nitrogen atmosphere means that the reaction flask was connected with a nitrogen balloon with a volume of about 1 L.

Hydrogen atmosphere means that the reaction flask was connected with a hydrogen balloon with a volume of about 1 L.

Hydrogenation reaction was usually vacuumized, filled with hydrogen, and repeated for 3 times.

Unless otherwise stated in Examples, the reaction was carried out in nitrogen atmosphere.

Unless otherwise stated in Examples, the solution was an aqueous solution.

Unless otherwise stated in Examples, the reaction temperature was room temperature, and the most suitable reaction temperature for room temperature was 20° C.-30° C.

DCM: dichloromethane;
EA: ethyl acetate;
HCl: hydrochloric acid;
THF: tetrahydrofuran;
DMF: N,N-dimethyl formamide;
PE: petroleum ether;
TLC: Thin layer chromatography;
SFC: supercritical fluid chromatography;
NCS: N-chlorosuccinimide;
Pd(dppf)Cl$_2$: [1,1'-bis (diphenylphosphine) ferrocene] palladium dichloride.

EXAMPLES

The technical solution of the present application will be illustrated by the following Examples in detail, and the scope of the present application comprises, but is not limited to the examples.

Example 1

Isopropyl((ethoxycarbonyl)(((6aR,10aR)-6,6,9-trimethyl-3-pentyl-6a,7,8,10a-tetrahydro-6H-benzo[c]chromen-1-yl)oxy)phosphoryl)-L-alaninate, Compound 1

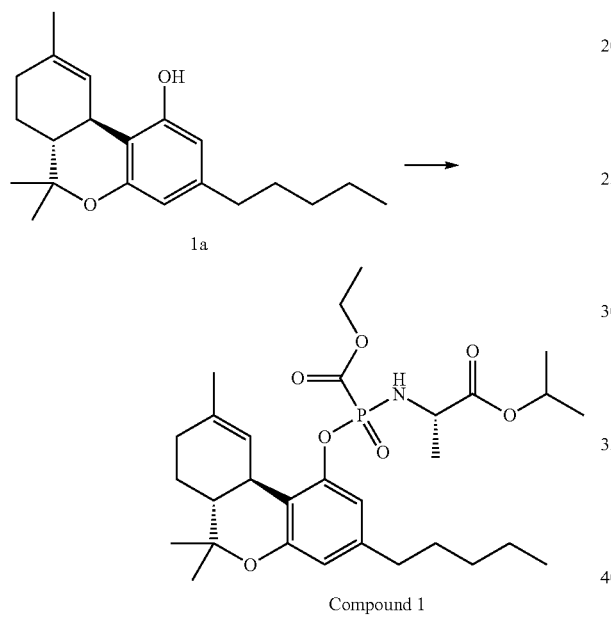

In a dry round-bottom flask, (6aR,10aR)-6,6,9-trimethyl-3-pentyl-6a,7,8,10a-tetrahydro-6H-benzo[c]chromen-1-ol 1a (0.78 g, 1.6 mmol, 1.0 eq.) was dissolved in dichloromethane (5 mL), followed by adding triethylamine (0.45 mL, 2.0 eq.). The round-bottom flask was placed in a reaction bath at −60° C., followed by adding ethyl(dichlorophosphoryl)formate (0.31 g, 1.6 mmol, 1.0 eq.) in dichloromethane (1 mL) and stirred at −60° C. for 1.5 hours. Then triethylamine (0.25 mL, 1.1 eq.) was added dropwise, followed by adding isopropyl L-alaninate hydrochloride (0.3 g, 1.6 mmol, 1.0 eq.) in dichloromethane (1 mL) and then the resultant mixture was warmed up naturally to room temperature and stirred overnight. Saturated solution of ammonium chloride was added at 0° C., and then the thus obtained mixture was extracted with dichloromethane. The resultant organic phase was dried over sodium sulfate and dried by rotary evaporator. The crude product was separated and purified by silica gel column chromatography (petroleum ether: ethyl acetate (v/v)=10:1) to obtain isopropyl((ethoxycarbonyl)(((6aR,10aR)-6,6,9-trimethyl-3-pentyl-6a,7,8,10a-tetrahydro-6H-benzo[c]chromen-1-yl)oxy)phosphoryl)-L-alaninate, compound 1 (128 mg, with a yield of 15%, yellow oil).

$^1$H NMR (300 MHz, Chloroform-d) δ 6.79 (t, 1H), 6.52-6.42 (m, 1H), 6.18-6.07 (m, 1H), 5.07-4.99 (m, 1H), 4.36-4.15 (m, 1H), 4.21-4.08 (m, 2H), 3.83-3.69 (m, 1H), 3.30 (d, 1H), 2.54-2.36 (m, 2H), 2.24-2.06 (m, 3H), 2.00-1.82 (m, 1H), 1.76-1.60 (m, 6H), 1.53 (t, 1H), 1.48-1.35 (m, 6H), 1.29-1.23 (m, 8H), 1.17-1.11 (m, 3H), 1.06 (s, 3H), 0.90-0.83 (m, 4H).

$^{31}$P NMR (121 MHz, Chloroform-d) δ-2.85.

LC-MS m/s (ESI)=564.30[M+1].

Example 2

Isopropyl((isopropoxycarbonyl)(((6aR,10aR)-6,6,9-trimethyl-3-pentyl-6a,7,8,10a-tetrahydro-6H-benzo[c]chromen-1-yl)oxy)phosphoryl)-L-alaninate, Compound 2

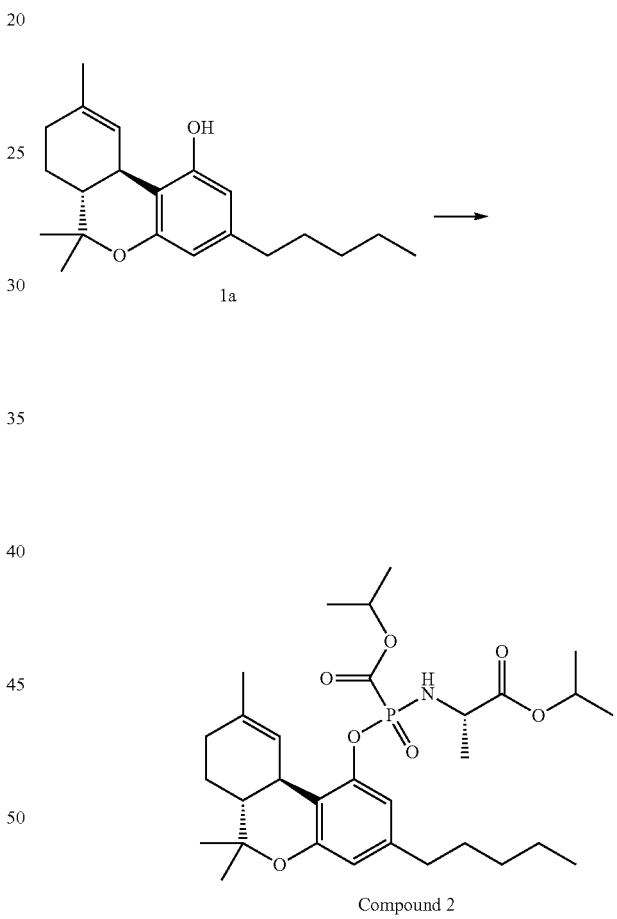

The target compound 2 (130 mg, with a yield of 16%, yellow oil) was prepared by the same method as that of compound 1.

$^1$H NMR (300 MHz, Chloroform-d) δ 6.79 (d, 1H), 6.50-6.42 (m, 1H), 6.14-6.11 (m, 1H), 5.13-4.89 (m, 2H), 4.37-4.16 (m, 1H), 3.79-3.71 (m, 1H), 3.30 (d, 1H), 2.50-2.40 (t, 2H), 2.16 (d, 2H), 1.98-1.83 (m, 1H), 1.67 (d, 4H), 1.54 (t, 1H), 1.43 (d, 3H), 1.40 (s, 3H), 1.34-1.13 (m, 15H), 1.09-1.02 (m, 6H), 0.92-0.79 (m, 3H).

$^{31}$P NMR (121 MHz, Chloroform-d) δ-2.77.

LC-MS m/s (ESI)=578.32[M+1].

Example 3

Isopropyl 2-(((ethoxycarbonyl)(((6aR,10aR)-6,6,9-trimethyl-3-pentyl-6a,7,8,10a-tetrahydro-6H-benzo[c]chromen-1-yl)oxy)phosphoryl)amino)-2-methylpropanoate, Compound 3

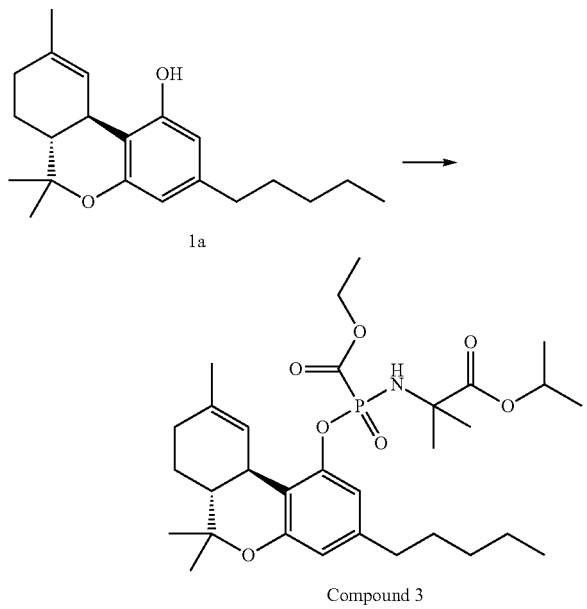

Compound 3

The target compound 3 (125 mg, with a yield of 14%, yellow oil) was prepared by the same method as that of compound 1.

¹H NMR (300 MHz, Chloroform-d) δ 6.77 (t, 1H), 6.46 (m, 1H), 6.17-6.15 (m, 1H), 5.08-4.99 (m, 1H), 4.35-4.09 (m, 3H), 3.33 (d, 1H), 2.51-2.39 (m, 2H), 2.19-2.08 (m, 2H), 1.96-1.82 (m, 1H), 1.70-1.65 (m, 4H), 1.63 (s, 3H), 1.57 (s, 4H), 1.52-1.40 (m, 1H), 1.39 (s, 3H), 1.37-1.32 (m, 1H), 1.31-1.27 (m, 3H), 1.27-1.22 (m, 6H), 1.21 (d, 1H), 1.19 (d, 2H), 1.17 (t, 1H), 1.07 (s, 3H), 0.93-0.80 (m, 3H).

³¹P NMR (121 MHz, Chloroform-d) δ-2.78.

LC-MS m/s (ESI)=578.32[M+1].

Example 4

Isopropyl 2-(((isopropoxycarbonyl)(((6aR,10aR)-6,6,9-trimethyl-3-pentyl-6a,7,8,10a-tetrahydro-6H-benzo[c]chromen-1-yl)oxy)phosphoryl)amino)-2-methylpropanoate, Compound 4

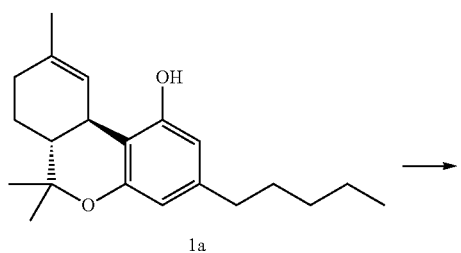

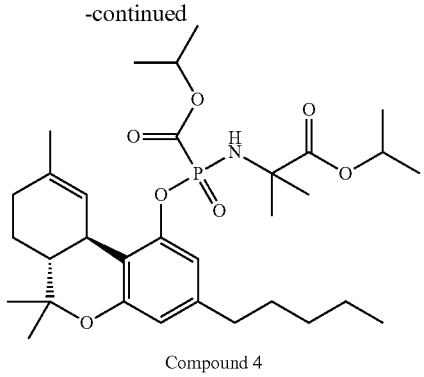

Compound 4

The target compound 4 (126 mg, with a yield of 15%, yellow oil) was prepared by the same method as that of compound 1.

¹H NMR (300 MHz, Chloroform-d) δ 6.75 (t, 1H), 6.42 (d, 1H), 6.15-6.13 (m, 1H), 5.11-4.90 (m, 2H), 4.19 (d, 1H), 3.30 (d, 1H), 2.48-2.36 (m, 2H), 2.15-2.05 (m, 2H), 1.98-1.78 (m, 1H), 1.67-1.61 (m, 4H), 1.59 (s, 3H), 1.54 (s, 3H), 1.53-1.46 (m, 2H), 1.45-1.37 (m, 1H), 1.36 (s, 3H), 1.29 (d, 2H), 1.25 (d, 2H), 1.23-1.19 (m, 9H), 1.10-1.08 (m, 3H), 1.04 (s, 3H), 0.89-0.77 (m, 3H).

³¹P NMR (121 MHz, Chloroform-d) δ-2.60.

LC-MS m/s (ESI)=592.33[M+1].

Example 5

Ethyl ((isopropoxycarbonyl)(((6aR,10aR)-6,6,9-trimethyl-3-pentyl-6a,7,8,10a-tetrahydro-6H-benzo[c]chromen-1-yl)oxy)phosphoryl)-L-alaninate, Compound 5

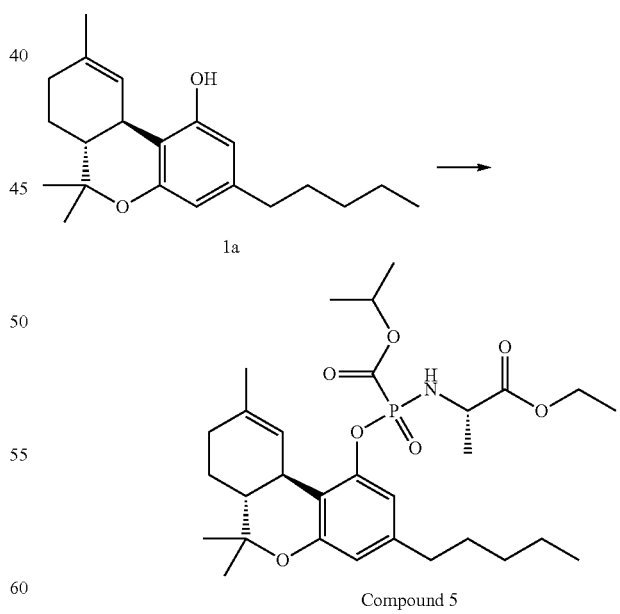

Compound 5

The target compound 5 (130 mg, with a yield of 8%, yellow oil) was prepared by the same method as that of compound 1.

¹H NMR (300 MHz, Chloroform-d) δ 6.80 (t, 1H), 6.47 (t, 1H), 6.14-6.12 (m, 1H), 5.04-4.95 (m, 1H), 4.40-4.10 (m, 3H), 3.81-3.67 (m, 1H), 3.29 (d, 1H), 2.48-2.42 (m, 2H), 2.16 (d, 2H), 1.71-1.67 (m, 4H), 1.61 (s, 2H), 1.58-1.51 (m, 2H), 1.46 (d, 3H), 1.40 (s, 3H), 1.31-1.24 (m, 7H), 1.21-1.18 (m, 3H), 1.07 (s, 3H), 1.06-1.03 (m, 3H), 0.92-0.81 (m, 3H).
$^{31}$P NMR (121 MHz, Chloroform-d) δ-2.87.
LC-MS m/s (ESI)=564.30[M+1].
According to the synthesis method disclosed in US20100152283, WO2020165902, WO2020252277, *Bioorg. Med. Chem.* 2010, 18, 7809-7815 and a book with ISBN: 978-0-470-84289-8, the following fragments 8a-20a and 22a were synthesized.
13a
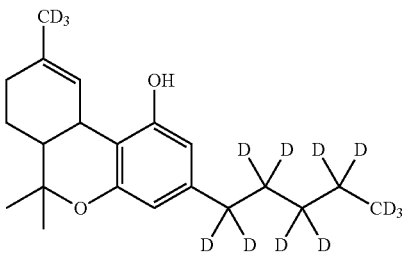
8a
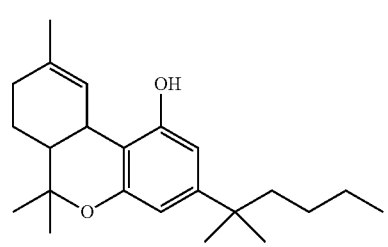
14a
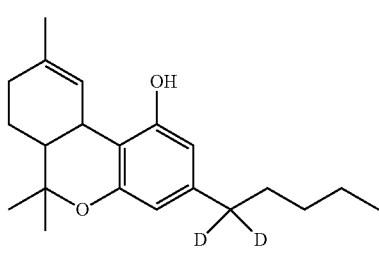
9a
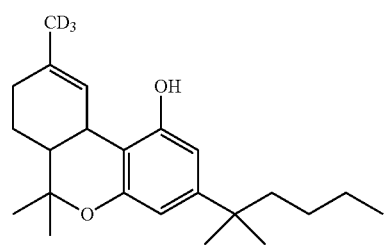
15a
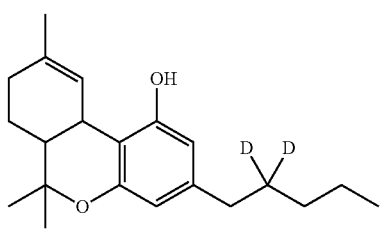
10a
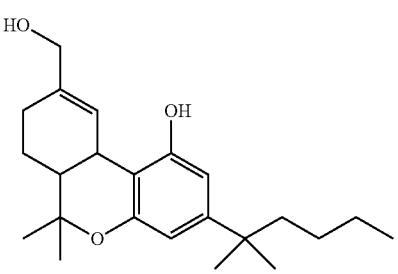
16a
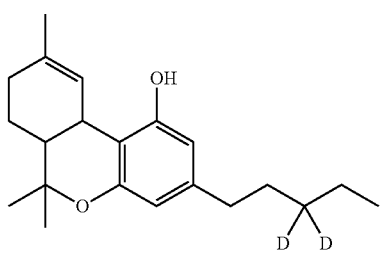
11a
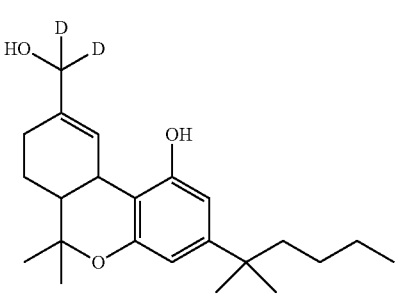
17a
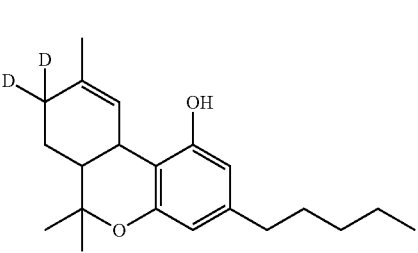
12a
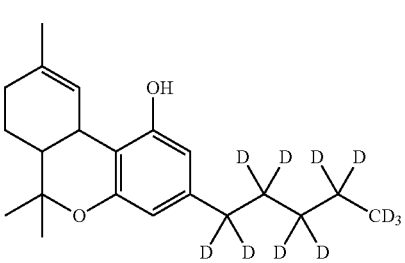
18a
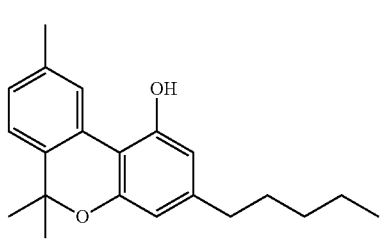

-continued
19a
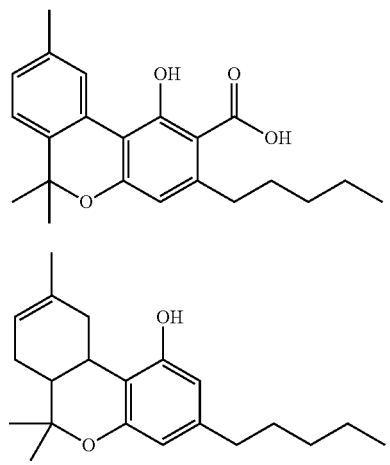
20a
-continued
22a
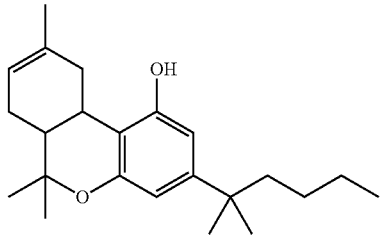
The following compounds were prepared using the same method as that of compound 1.
| No. | Structural formula | [M + 1]+ |
|---|---|---|
| Compound 6 | | 536.6 |
| Compound 7 | | 564.7 |
| Compound 8 | | 592.7 |

-continued
| No. | Structural formula | [M + 1]+ |
|---|---|---|
| Compound 9 | 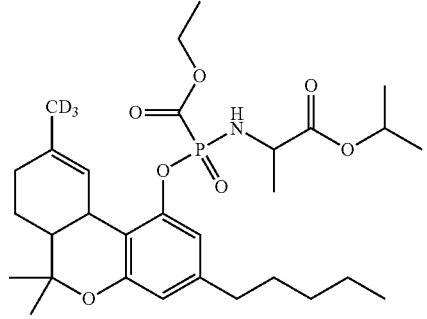 [SMILES: [2H]C([2H])([2H])C1=CC2c3c(cc(CCCCC)cc3OP(=O)(NC(C)C(=O)OC(C)C)C(=O)OCC)OC(C)(C)C2CC1] | 567.7 |
| Compound 10 | 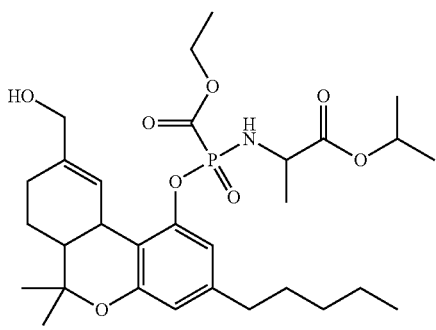 [SMILES: CCCCCc1cc2c(c(OP(=O)(NC(C)C(=O)OC(C)C)C(=O)OCC)c1)C1C=C(CO)CCC1C(C)(C)O2] | 580.7 |
| Compound 11 | 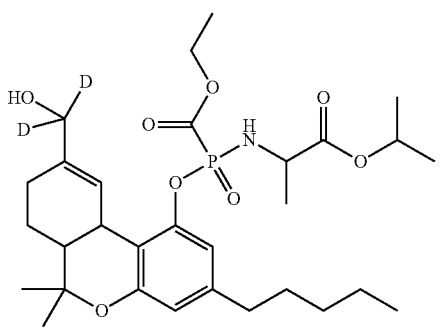 [SMILES: [2H]C([2H])(O)C1=CC2c3c(cc(CCCCC)cc3OP(=O)(NC(C)C(=O)OC(C)C)C(=O)OCC)OC(C)(C)C2CC1] | 582.7 |
| Compound 12 | 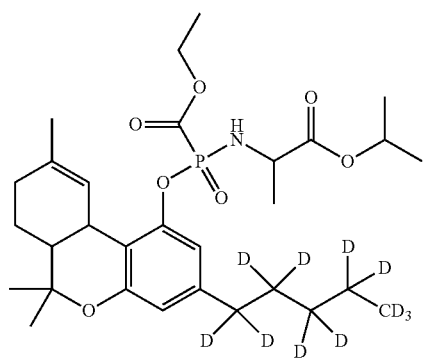 [SMILES: [2H]C([2H])([2H])C([2H])([2H])C([2H])([2H])C([2H])([2H])C([2H])([2H])c1cc2c(c(OP(=O)(NC(C)C(=O)OC(C)C)C(=O)OCC)c1)C1C=C(C)CCC1C(C)(C)O2] | 575.7 |

-continued

| No. | Structural formula | [M + 1]+ |
|---|---|---|
| Compound 13 | | 578.8 |
| Compound 14 | | 566.7 |
| Compound 15 | | 566.7 |
| Compound 16 | | 566.7 |

-continued
| No. | Structural formula | [M + 1]+ |
|---|---|---|
| Compound 17 | 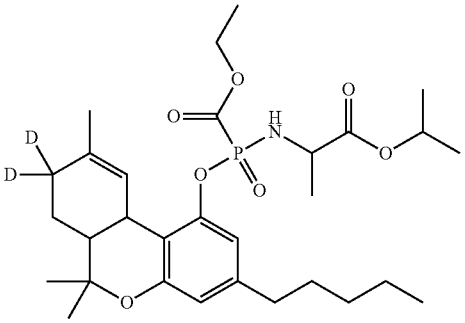 [SMILES: [2H]C1([2H])CC2C(C=C1C)c1c(cc(CCCCC)cc1OP(=O)(NC(C)C(=O)OC(C)C)C(=O)OCC)OC2(C)C] | 566.3 |
| Compound 18 | 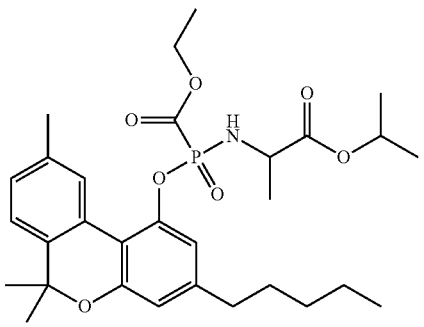 [SMILES: CCCCCc1cc2c(c(OP(=O)(NC(C)C(=O)OC(C)C)C(=O)OCC)c1)-c1cc(C)ccc1C(C)(C)O2] | 560.6 |
| Compound 19 | 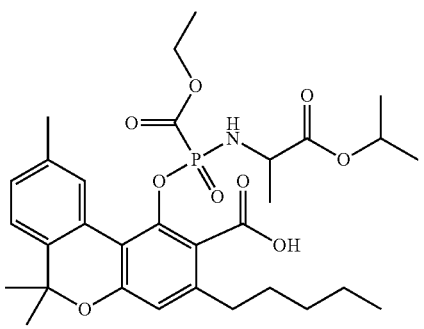 [SMILES: CCCCCc1cc2c(c(OP(=O)(NC(C)C(=O)OC(C)C)C(=O)OCC)c1C(=O)O)-c1cc(C)ccc1C(C)(C)O2] | 604.6 |
| Compound 20 | 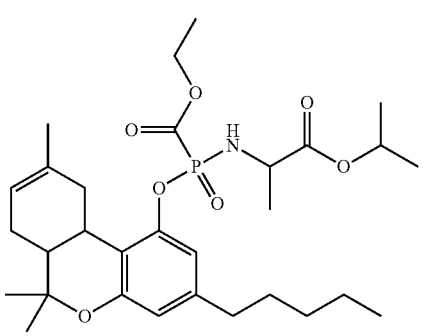 [SMILES: CCCCCc1cc2c(c(OP(=O)(NC(C)C(=O)OC(C)C)C(=O)OCC)c1)C1CC(C)=CCC1C(C)(C)O2] | 564.7 |
| Compound 21 | 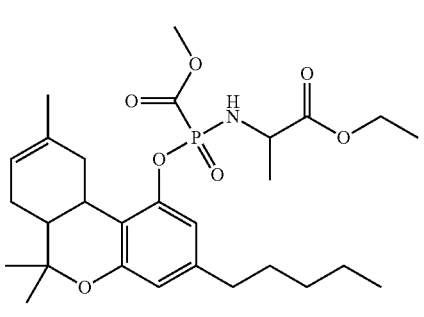 [SMILES: CCCCCc1cc2c(c(OP(=O)(NC(C)C(=O)OCC)C(=O)OC)c1)C1CC(C)=CCC1C(C)(C)O2] | 536.6 |

| No. | Structural formula | [M + 1]+ |
|---|---|---|
| Compound 22 | | 564.7 |

Pharmacokinetics in Rats

Healthy adult SD rats (n=3 per group) were fasted overnight (free access to water), and then were administrated the drugs by intragastric administration (i.g.) (10 mg/kg). 0.1 mL of blood was collected from jugular plexus of the rats at 30 minutes, 1 hour and 8 hour after administration. All blood samples were anticoagulated with $K_2EDTA$, then centrifuged at 3500 rpm at 5° C. for 10 minutes to separate plasma, and stored at −20° C. for test. Parent drug concentration in plasma was determined by LC/MS/MS method. Using the above method, the blood drug concentration (ng/mL) of the parent drugs of the compounds at each time point in the rats were measured, the results are as follows:

| No. | Administration dose | Parent drug | 30 min | 1 h | 8 h |
|---|---|---|---|---|---|
| Compound 1 | 10 mg/kg | THC | 274.4 | 536.1 | 38.7 |
| Compound 8 | 10 mg/kg | 8a | 184.6 | 483.4 | 25.9 |
| Compound 9 | 10 mg/kg | 9a | 367.8 | 457.8 | 51.4 |
| Compound 11 | 10 mg/kg | 11a | 128.0 | 591.7 | 58.6 |
| Compound 13 | 10 mg/kg | 13a | 308.9 | 498.4 | 69.4 |
| Compound 18 | 10 mg/kg | 18a | 458.9 | 1044.1 | 63.2 |

Experiment results showed that the parent drugs can respectively be detected in plasma after intragastric administration of compounds of the present application, which indicates that the compounds of the present application can be absorbed orally, and the compounds can be quickly converted into the parent drugs in vivo, and they show better oral bioavailability than the parent drugs.

Although the specific embodiments are described in detail in the description of the present application, those skilled in the art should understand that the above embodiments are exemplary and cannot be understood as limitations to the present application. If those skilled in the art make improvements and modifications to the present application without departing from the principle of the present application, the technical solution obtained by these improvements and modifications shall also fall within the protection scope of the claims of the present application.

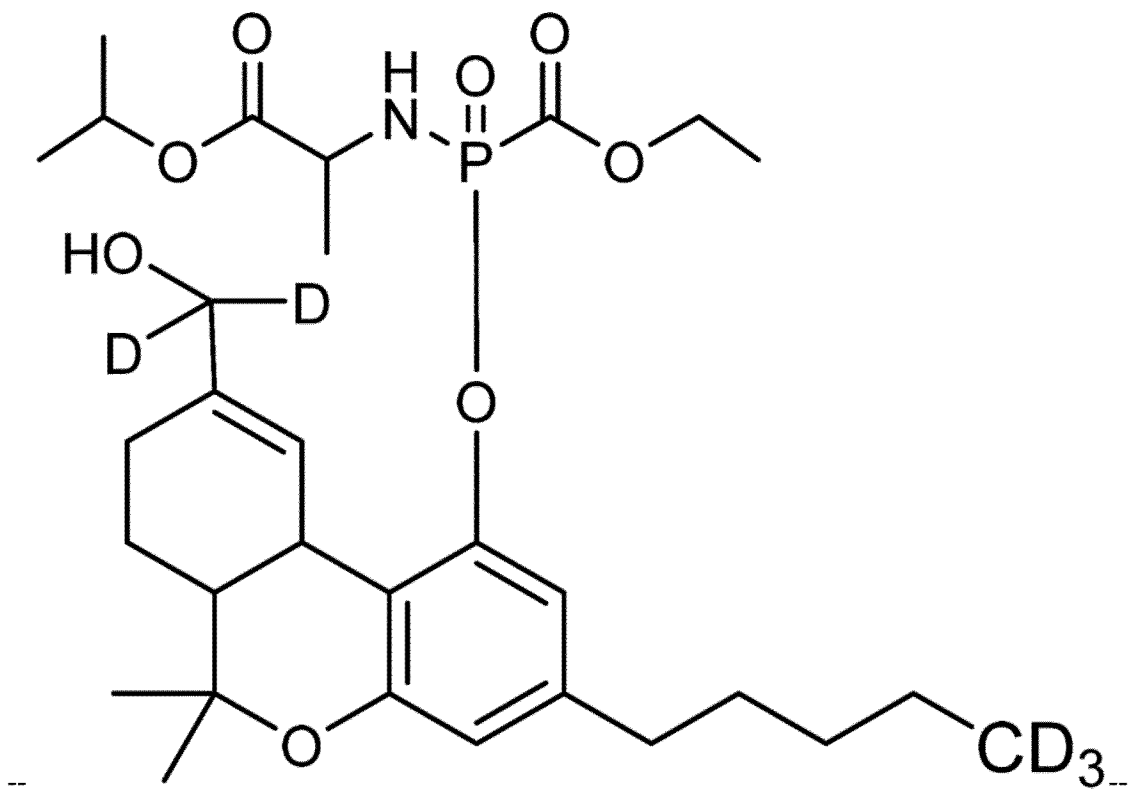

The invention claimed is:

1. A compound represented by general formula (I), or stereoisomers, solvates, metabolites, pharmaceutically acceptable salts or cocrystals thereof:

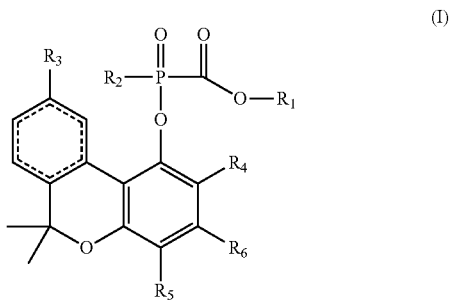

wherein:
$R_1$ is $C_{1-6}$ alkyl;
$R_2$ is

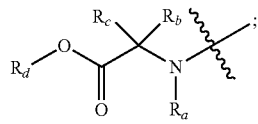

$R_3$ is selected from the group consisting of methyl, $C_{3-8}$ carbocyclic group, —$CH_2OH$, carboxyl, —C(=O)O$C_{1-6}$ alkyl and —C(=O)N$R^{b1}R^{b2}$;
$R_4$ and $R_5$ are each independently selected from the group consisting of H, halogen and carboxyl;
$R_a$ is selected from the group consisting of H and $C_{1-6}$ alkyl;
$R_b$ and $R_c$ are each independently selected from the group consisting of H, $C_{1-6}$ alkyl, amino acid side chain, —$C_{1-6}$ alkylene-$C_{3-12}$ carbocyclic ring and —$C_{1-6}$ alkylene-$C_{3-12}$ heterocyclic ring; the $C_{3-12}$ heterocyclic ring contains 1 to 4 heteroatoms selected from the group consisting of N, O and S; the $C_{1-6}$ alkylene, the $C_{1-6}$ alkyl, the $C_{3-12}$ carbocyclic ring and the $C_{3-12}$ heterocyclic ring are optionally further substituted by 0 to 3 substituents selected from the group consisting of hydroxyl, carboxyl, halogen, cyano, =O, $C_{1-6}$ alkyl, $C_{1-6}$ heteroalkyl, $C_{2-6}$ alkenyl, $C_{2-6}$ alkynyl, —N$R^{b1}R^{b2}$, —C(=O)O$C_{1-6}$ alkyl, —C(=O)N$R^{b1}R^{b2}$, $C_{3-12}$ cycloalkyl, $C_{3-12}$ heterocycloalkyl, $C_{6-12}$ aryl or $C_{5-12}$ heteroaryl; and the $C_{1-6}$ alkyl, the $C_{1-6}$ heteroalkyl, the $C_{2-6}$ alkenyl or the $C_{2-6}$ alkynyl are optionally further substituted by one or more groups selected from the group consisting of hydroxyl, carboxyl, cyano, halogen, —O—$R^{b1}$, —$NR^{b1}R^{b2}$, $C_{3-12}$ cycloalkyl, $C_{3-12}$ heterocycloalkyl, $C_{6-12}$ aryl and $C_{5-12}$ heteroaryl; when the amino acid side chain contains hydroxyl, mercapto or carboxyl, the hydroxyl, the mercapto or the carboxyl is optionally esterified;

$R^{b1}$ and $R^{b2}$ are each independently selected from the group consisting of H, $C_{1-6}$ alkyl, —C(=O)$R^{b3}$ and —C(=O)$NR^{b4}R^{b5}$, wherein the $C_{1-6}$ alkyl is optionally further substituted by one or more substituents selected from the group consisting of hydroxyl, halogen, $C_{1-6}$ alkyl, $C_{1-6}$ alkoxy, $C_{6-12}$ aryl, $C_{5-12}$ heteroaryl, $C_{3-12}$ cycloalkyl and $C_{3-12}$ heterocycloalkyl;

$R^{b3}$ is selected from the group consisting of $C_{1-6}$ alkyl, $C_{1-6}$ alkoxy and $C_{6-12}$ aryl;

$R^{b4}$ and $R^{b5}$ are each independently selected from the group consisting of H and $C_{1-6}$ alkyl; or $R^{b4}$ and $R^b$s together with N atom form a 3 to 12 membered heterocycle containing 1 to 4 heteroatoms selected from the group consisting of N, O and S;

or, $R_b$ and $R_c$ together with the atom to which they are attached form a 3 to 6 membered carbocyclic ring or a 3 to 6 membered heterocyclic ring, the 3 to 6 membered carbocyclic ring or the 3 to 6 membered heterocyclic ring is optionally further substituted by 0 to 3 substituents selected from the group consisting of F, Cl, Br, I, hydroxyl, carboxyl and amino, wherein the 3 to 6 membered heterocyclic ring contains 1 to 4 heteroatoms selected from the group consisting of N, O and S;

$R_d$ is selected from the group consisting of $C_{1-6}$ alkyl, $C_{2-6}$ alkenyl, $C_{2-6}$ alkynyl, $C_{3-10}$ carbocyclic ring, 3 to 10 membered heterocyclic ring, —$C_{1-6}$ alkylene-$C_{3-10}$ carbocyclic ring, —$C_{1-6}$ alkylene-3 to 10 membered heterocyclic ring, —$C_{1-6}$ alkylene-O—$C_{1-6}$ alkylene-$C_{3-10}$ carbocyclic ring, —$C_{1-6}$ alkylene-O—$C_{1-6}$ alkylene-3 to 10 heterocyclic ring and —$C_{1-6}$ alkylene-O—$C_{1-4}$ alkyl; the $C_{1-6}$ alkylene, the $C_{2-6}$ alkenyl, the $C_{2-6}$ alkynyl, the $C_{1-6}$ alkyl, the $C_{3-10}$ carbocyclic ring and the 3 to 10 membered heterocyclic ring are optionally further substituted with 0 to 4 substituents selected from the group consisting of H, F, Cl, Br, I, hydroxyl, carboxyl, amino, 1-cyclopropylethyl, $C_{1-4}$ alkyl, $C_{1-4}$ alkoxy, —OC(=O)$OR_{d1}$ and —OC(=O)$R_{d2}$, wherein the 3 to 10 membered heterocyclic ring contains 1 to 6 heteroatoms selected from the group consisting of N, O and S;

$R_{d1}$ and $R_{d2}$ are each independently selected from the group consisting of $C_{1-4}$ alkyl, $C_{3-10}$ carbocyclic ring and 3 to 10 membered heterocyclic ring, the $C_{1-4}$ alkyl, the $C_{3-10}$ carbocyclic ring or the 3 to 10 membered heterocyclic ring is optionally further substituted with 0 to 4 substituents selected from the group consisting of H, F, Cl, Br, I, hydroxyl, carboxyl, $C_{1-4}$ alkyl, $C_{1-4}$ alkoxy, $C_{3-10}$ carbocyclic ring and 3 to 10 membered heterocylic ring, wherein the 3 to 10 membered heterocylic ring contains 1 to 6 heteroatoms selected from the group consisting of N, O and S;

$R_6$ is selected from the group consisting of $C_{1-12}$ alkyl, $C_{1-12}$ heteroalkyl, $C_{2-12}$ alkenyl, $C_{2-12}$ alkynyl, $C_{1-12}$ alkylene, $C_{3-12}$ carbocyclic group, $C_{3-12}$ heterocyclic group, —$C_{1-6}$ alkylene-$C_{3-12}$ carbocyclic group, —$C_{1-6}$ alkylene-$C_{3-12}$ heterocyclic group, —$NR^{b1}R^{b2}$, —$C_{1-6}$ alkylene-C(=O)O$C_{1-6}$ alkyl and —$C_{1-6}$ alkylene-C(=O)$N^{b1}R^{b2}$, wherein the $C_{1-12}$ alkyl, the $C_{1-12}$ heteroalkyl, the $C_{2-12}$ alkenyl, the $C_{2-12}$ alkynyl, $C_{1-12}$ alkylene, the $C_{3-12}$ carbocyclic group and the $C_{3-12}$ heterocyclic group are optionally substituted with one or more substituents selected from the group consisting of hydroxyl, carboxyl, halogen, cyano, =O, $C_{1-6}$ alkyl, —$NR^{b1}R^{b2}$, $C_{3-12}$ carbocyclic group, $C_{3-12}$ heterocyclic group, $C_{2-6}$ alkenyl, $C_{2-6}$ alkynyl, —C(=O)O$C_{1-6}$ alkyl, —C(=O)$C_{1-6}$ alkyl, —C(=O)$NR^{b1}R^{b2}$, —S(=O)$C_{1-6}$ alkyl and —S(=O)$_2C_{1-6}$ alkyl, wherein as substituents, the $C_{1-6}$ alkyl, the $C_{3-12}$ carbocyclic group and the $C_{3-12}$ heterocyclic group are optionally further substituted with one or more substituents selected from the group consisting of =O, hydroxyl, carboxyl, halogen, cyano, —C(=O)O$C_{1-6}$ alkyl and —C(=O)$C_{1-6}$ alkyl;

=== is a single bond or a double bond;

or, the general formula (I) is optionally substituted with one or more D atoms.

2. The compound, or stereoisomers, solvates, metabolites, pharmaceutically acceptable salts or cocrystals thereof according to claim 1, wherein the compound is represented by general formula (II):

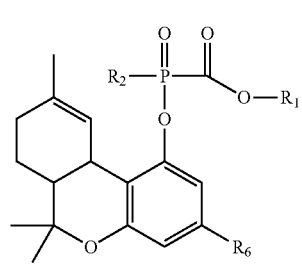

(II)

wherein,
$R_1$ is $C_{1-6}$ alkyl;
$R_2$ is

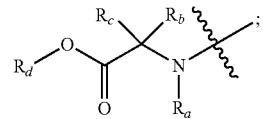

;

$R_a$ is H;
$R_b$ and $R_c$ are each independently selected from the group consisting of H and amino acid side chain; when the amino acid side chain contains hydroxyl, mercapto or carboxyl, the hydroxyl, the mercapto or the carboxyl is optionally esterified;

$R_d$ is selected from the group consisting of $C_{1-6}$ alkyl, —$C_{3-10}$ carbocyclic ring and 3 to 10 membered heterocyclic ring, and the $C_{1-6}$ alkyl, the —$C_{3-10}$ carbocyclic ring or the 3 to 10 membered heterocyclic ring is optionally further substituted with 0 to 4 substituents selected from the group consisting of H, F, Cl, Br, I, hydroxyl, carboxyl, amino, 1-cyclopropylethyl, $C_{1-4}$ alkyl, $C_{1-4}$ alkoxy, —OC(=O)$OR_{d1}$ and —OC(=O)$R_{d2}$, wherein the 3 to 10 membered heterocyclic ring contains 1 to 6 heteroatoms selected from the group consisting of N, O and S;

$R_{d1}$ and $R_{d2}$ are each independently $C_{1-4}$ alkyl;

$R_6$ is selected from the group consisting of $C_{1-12}$ alkyl, $C_{3-12}$ carbocyclic group, and $C_{3-12}$ heterocyclic group, wherein the $C_{1-12}$ alkyl, the $C_{3-12}$ carbocyclic group and the $C_{3-12}$ heterocyclic group are optionally substituted by one or more substituents selected from the group consisting of hydroxyl, carboxyl, halogen, cyano, =O, C$_{1-6}$ alkyl, —NR$^{b1}$R$^{b2}$, C$_{3-12}$ carbocyclic group, C$_{3-12}$ heterocyclic group, C$_{2-6}$ alkenyl group, C$_{2-6}$ alkynyl group, —C(=O)OC$_{1-6}$ alkyl, —C(=O)C$_{1-6}$ alkyl, —C(=O)NR$^{b1}$R$^{b2}$, —S(=O)C$_{1-6}$ alkyl and —S(=O)$_2$C$_{1-6}$ alkyl, wherein as substituents, the C$_{1-6}$ alkyl, the C$_{3-12}$ carbocylic group, the C$_{3-12}$ heterocyclic group are optionally substituted by one or more substituents selected from the group consisting of =O, hydroxyl, carboxyl, halogen, cyano, —C(=O)OC$_{1-6}$ alkyl and —C(=O)C$_{1-6}$ alkyl;

R$^{b1}$ and R$^{b2}$ are each independently selected from the group consisting of H, C$_{1-6}$ alkyl, —C(=O)R$^{b3}$ and —C(=O)NR$^{b4}$R$^{b5}$, wherein the C$_{1-6}$ alkyl is optionally further substituted by one or more substituents selected from the group consisting of hydroxyl, halogen, C$_{1-6}$ alkyl, C$_{1-6}$ alkoxy, C$_{6-12}$ aryl, C$_{5-12}$ heteroaryl, C$_{3-12}$ cycloalkyl and C$_{3-12}$ heterocycloalkyl;

R$^{b3}$ is selected from the group consisting of C$_{1-6}$ alkyl, C$_{1-6}$ alkoxy and C$_{6-12}$ aryl;

R$^{b4}$ and R$^{b5}$ are each independently selected from the group consisting of H and C$_{1-6}$ alkyl; or R$^{b4}$ and R$^{b5}$ together with N atom form a 3 to 12 membered heterocyclic ring containing 1 to 4 heteroatoms selected from the group consisting of N, O and S;

or, the general formula (II) is optionally substituted with one or more D atoms.

3. The compound, or stereoisomers, solvates, metabolites, pharmaceutically acceptable salts or cocrystals thereof according to claim 2, wherein the compound is represented by general formula (III):

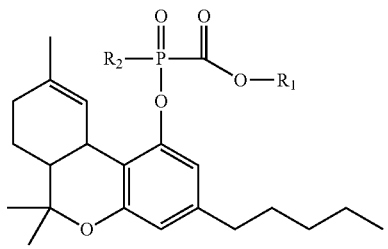

(III)

wherein,
R$_1$ is C$_{1-6}$ alkyl;
R$_2$ is

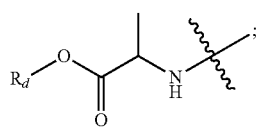

R$_d$ is selected from the group consisting of C$_{1-6}$ alkyl, C$_{3-10}$ carbocyclic ring and 3 to 10 membered heterocyclic ring, wherein the C$_{1-6}$ alkyl, the C$_{3-10}$ carbocyclic ring or the 3 to 10 membered heterocyclic ring is optionally further substituted with 0 to 4 substituents selected from the group consisting of H, F, Cl, Br, I, hydroxyl, carboxyl, amino, 1-cyclopropylethyl, C$_{1-4}$ alkyl, C$_{1-4}$ alkoxy, —OC(=O)OR$_{d1}$ and —OC(=O)R$_{d2}$, wherein the 3 to 10 membered heterocyclic ring contains 1 to 6 heteroatoms selected from the group consisting of N, O and S;

R$_{d1}$ and R$_{d2}$ are each independently C$_{1-4}$ alkyl;
or, the general formula (III) is optionally substituted with one or more D atoms.

4. The compound, or stereoisomers, solvates, metabolites, pharmaceutically acceptable salts or cocrystals thereof according to claim 3, wherein the compound has one of the following structures:

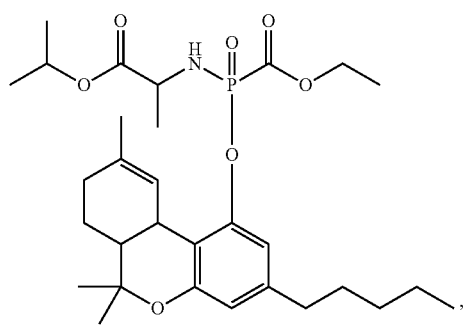

,

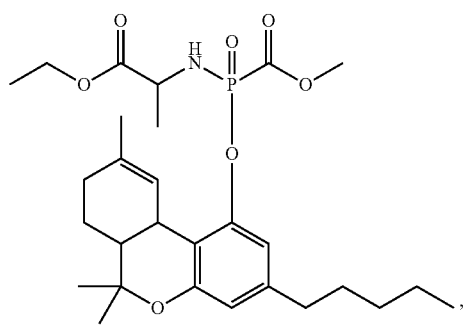

,

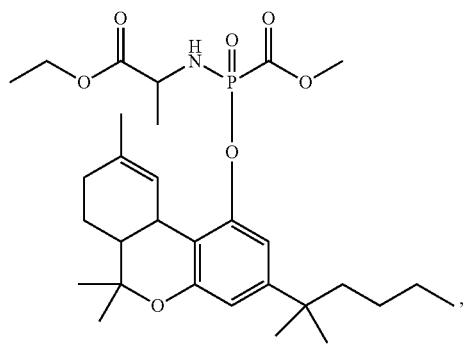

,

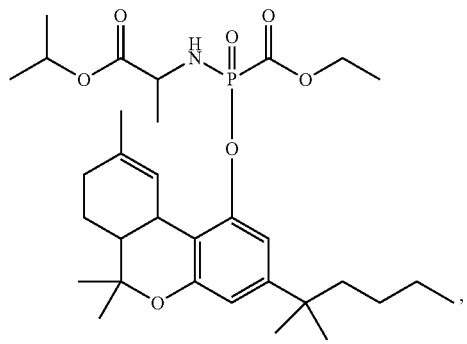

,

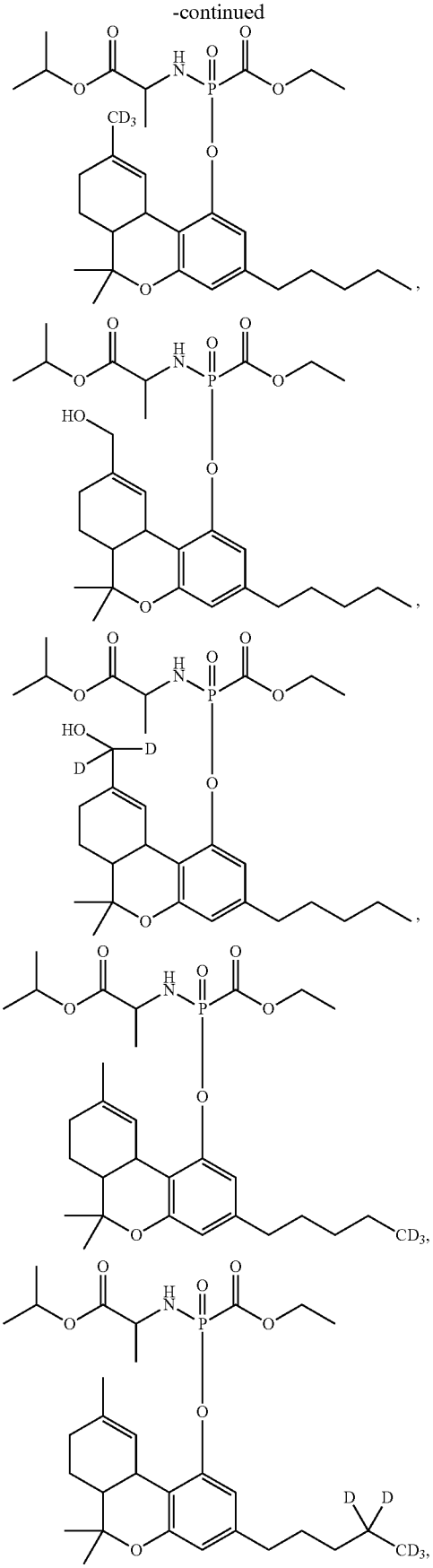
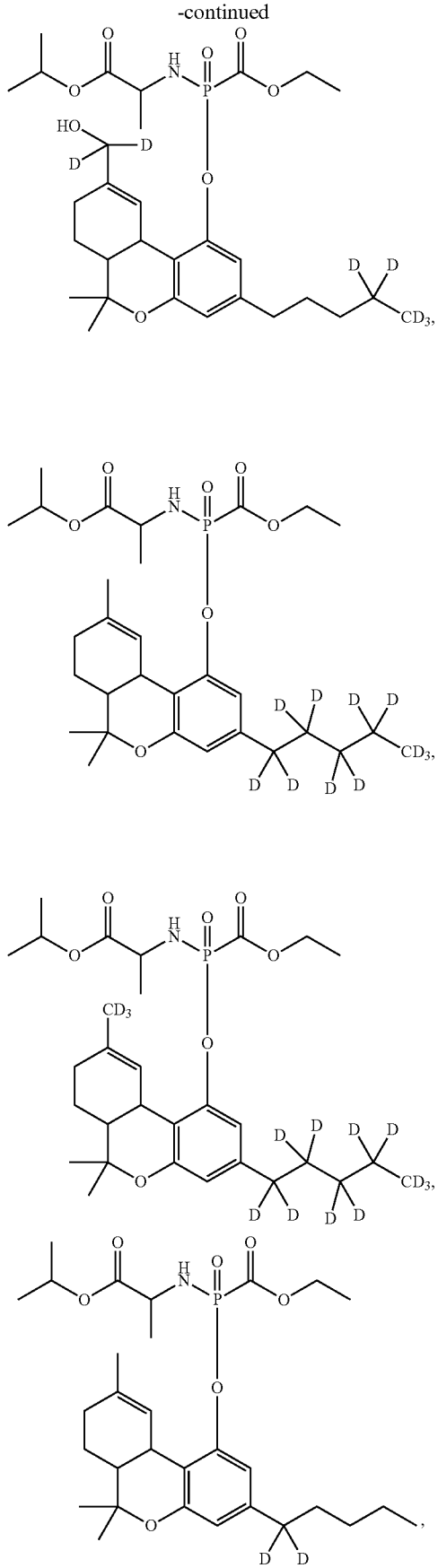

-continued
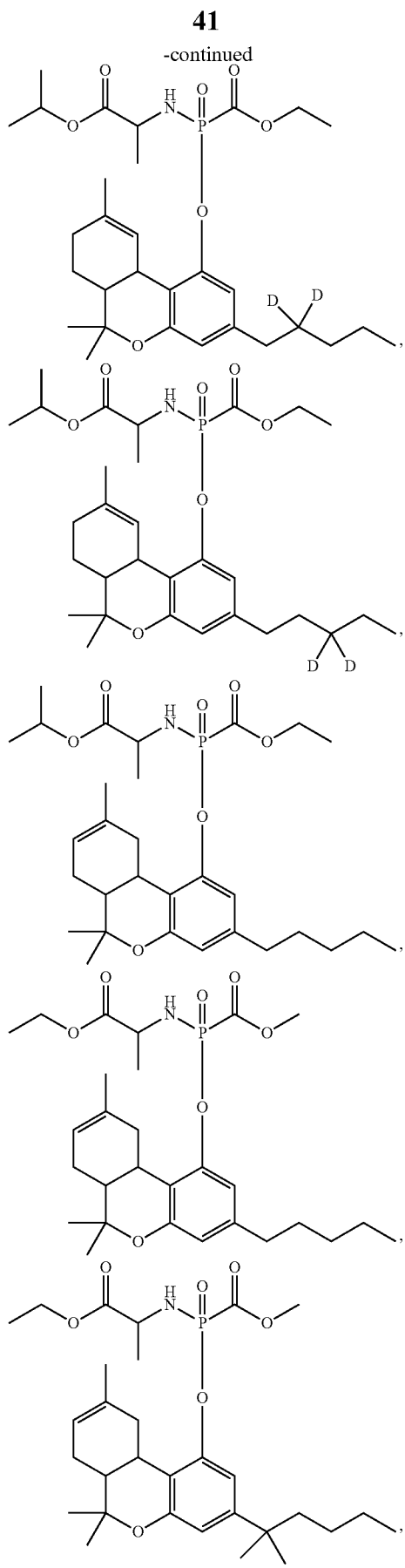
-continued
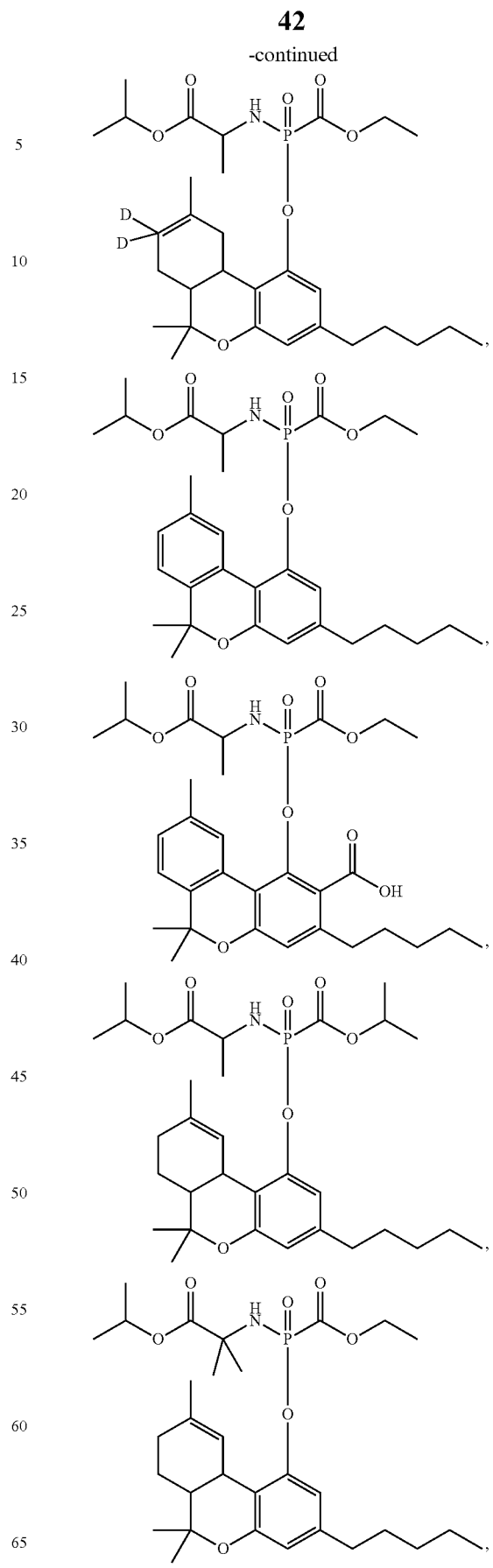

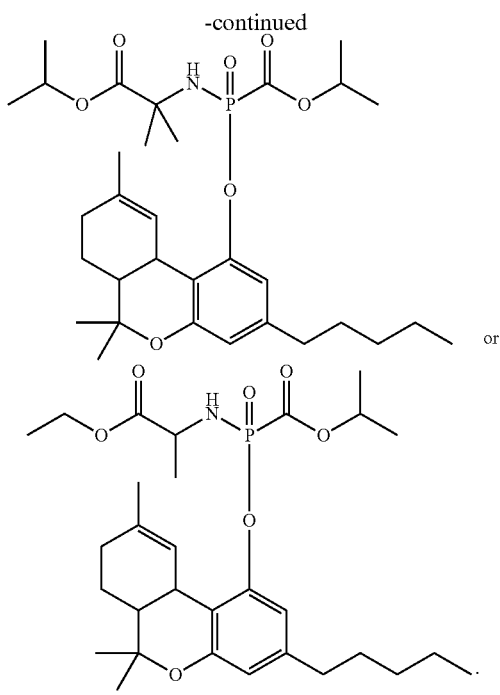

5. A pharmaceutical composition comprising:
   (1) the compound, or stereoisomers, solvates, metabolites, pharmaceutically acceptable salts or cocrystals thereof according to claim 4,
   (2) optional one or more other active ingredients; and
   (3) a pharmaceutically acceptable carrier and/or excipient.

6. The pharmaceutical composition according to claim 5, wherein, the other active ingredient is one or more selected from the group consisting of ginkgolides, antineoplastic agents, anticoagulants, antiepileptic agents, antidepressants, anxiolytics, hypnotics, analgesics and anesthetics, or stereoisomers, metabolites, hydrates, solvates, pharmaceutically acceptable salts or cocrystals of the other active ingredients; preferably, the ginkgolides are one selected from the group consisting of ginkgolides A, ginkgolides B, ginkgolides C, ginkgolides D, ginkgolides J, ginkgolides M, ginkgolides K, ginkgolides L, ginkgolides N, ginkgolide P, ginkgolide Q and bilobalide or combinations of two or more thereof in any ratio.

7. A method for treating post-traumatic stress disorder, facial paralysis, stroke, migraine, coronary heart disease stable angina pectoris, cerebral infarction, thromboembolism, myocardial infarction, cardiac ischemia, coronary artery disease, hypertension, cerebral ischemia, improvement of sexual function, spasm, acute and chronic pain, fibromyalgia, postoperative pain, cluster headache, tension headache, back pain, limb pain, lumbago, neck pain, neuropathic pain, cancer pain, trigeminal neuralgia, arthritic pain, inflammatory pain, Dravet syndrome, Lennox-Gastaut syndrome, Prader-Willi syndrome, Sturge-Weber syndrome, fragile X syndrome, anxiety, bipolar affective disorder, autism, general anxiety disorder, social anxiety disorder, epilepsy, Parkinson's disease, Alzheimer's disease, Huntington's disease, opioid abuse, alcoholism, nicotine addiction, anorexia, cachexia, chemotherapy-related nausea and vomiting, postoperative nausea and vomiting, amyotrophic lateral sclerosis (ALS), Friedreich ataxia, schizophrenia, obsessive-compulsive disorder, multiple sclerosis, depression, sleep disorder, spasm caused by multiple sclerosis, dysmyotonia, sleep apnea, paralytic dementia, hypomnesis or glioblastoma, wherein the method comprises administering to a subject in need thereof a therapeutically effective amount of the compound of claim 1, or stereoisomers, solvates, metabolites, pharmaceutically acceptable salts or cocrystals thereof.

\* \* \* \* \*

UNITED STATES PATENT AND TRADEMARK OFFICE
CERTIFICATE OF CORRECTION

PATENT NO. : 12,391,711 B2
APPLICATION NO. : 17/772993
DATED : August 19, 2025
INVENTOR(S) : Jing Zhang et al.

Page 1 of 2

It is certified that error appears in the above-identified patent and that said Letters Patent is hereby corrected as shown below:

In the Claims

Column 34, Claim 1, Line 62:
"–C(=O)N$^{b1}$R$^{b2}$," should read: -- –C(=O)NR$^{b1}$R$^{b2}$, --

Column 35, Claim 1, Lines 62-63:
"–C$_{1-6}$ alkylene-C(=O)N$^{b1}$R$^{b2}$" should read: -- –C$_{1-6}$ alkylene-C(=O)NR$^{b1}$R$^{b2}$, --

Column 40, Claim 4, Lines 1-15:
"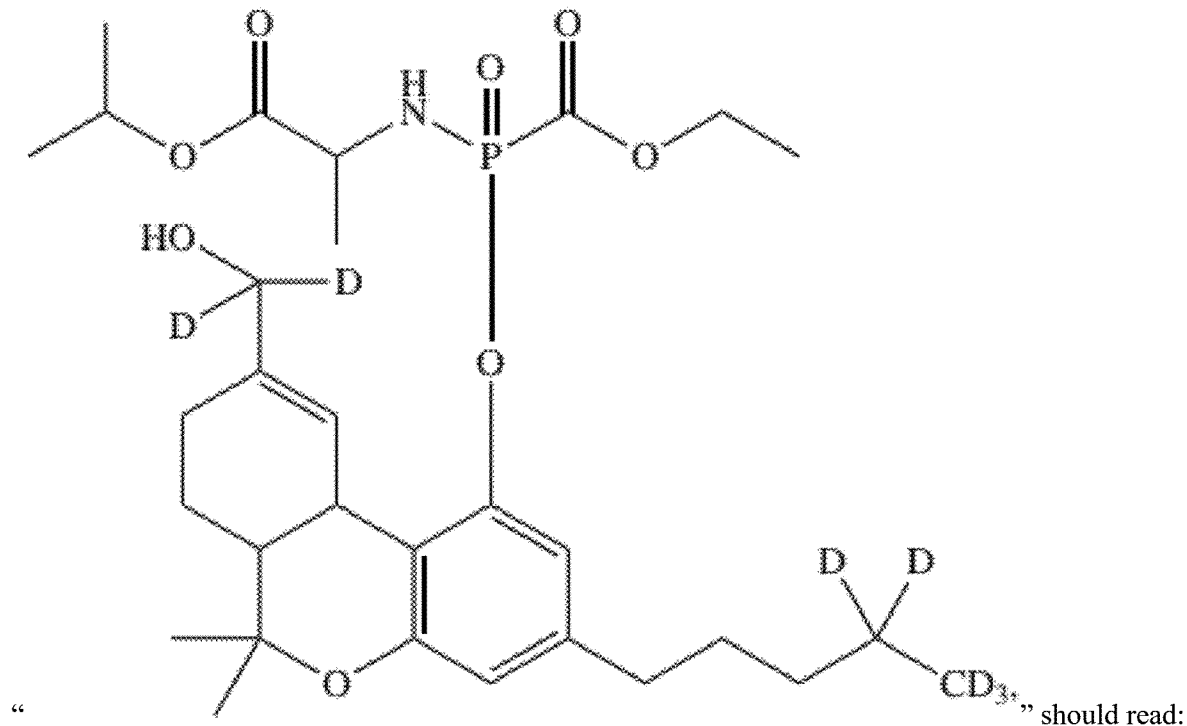" should read:

Signed and Sealed this
Eighteenth Day of November, 2025

John A. Squires
*Director of the United States Patent and Trademark Office*